US012586679B2

(12) United States Patent

Jensen et al.

(10) Patent No.: US 12,586,679 B2

(45) Date of Patent: Mar. 24, 2026

(54) SYSTEMS AND METHODS FOR ASSESSING BAYS ON DIAGNOSTIC DEVICES

(71) Applicant: ROCHE MOLECULAR SYSTEMS, INC., Pleasanton, CA (US)

(72) Inventors: Tyler David Jensen, Carlsbad, CA (US); Michael Nguyen, Carlsbad, CA (US); Dustin K. Harshman, Carlsbad, CA (US)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 605 days.

(21) Appl. No.: 17/928,584

(22) PCT Filed: Jun. 11, 2021

(86) PCT No.: PCT/US2021/037051

§ 371 (c)(1),
(2) Date: Nov. 29, 2022

(87) PCT Pub. No.: WO2021/252923

PCT Pub. Date: Dec. 16, 2021

(65) Prior Publication Data

US 2023/0352159 A1     Nov. 2, 2023

Related U.S. Application Data

(60) Provisional application No. 63/038,613, filed on Jun. 12, 2020.

(51) Int. Cl.
G16H 40/40 (2018.01)
G01N 35/00 (2006.01)

(52) U.S. Cl.
CPC ....... G16H 40/40 (2018.01); G01N 35/00722 (2013.01); G01N 2035/0091 (2013.01)

(58) Field of Classification Search
CPC ........ G16H 40/40; G16H 40/00; G16H 10/40; G16H 15/00; G16H 40/63; G16H 40/67;
(Continued)

(56) References Cited

U.S. PATENT DOCUMENTS 4,225,410 A     9/1980  Pace
4,469,863 A     9/1984  Ts'o et al.
(Continued)

FOREIGN PATENT DOCUMENTS

CA          3036572 A1     3/2018
DE     102005032134 A1     1/2007
(Continued)

OTHER PUBLICATIONS

International Search Report and Written Opinion PCT/US2021/037051 (Nov. 10, 2021) 11pp.
(Continued)

*Primary Examiner* — Mohamed Charioui
(74) *Attorney, Agent, or Firm* — Snell & Wilmer, L.L.P.; April Wurster

(57) ABSTRACT

Disclosed are methods, systems and apparatuses in which a diagnostic instrument analyzes data collected over time, and based on that information, disables a bay, suggests a bay, puts a bay on standby or combinations thereof. In some embodiments, the method, system and apparatus allows the diagnostic instrument to have higher validity rates in the field and allows the provider to set up service calls, schedule maintenance and perform remote maintenance, as well as other functions based on the data collected over time.

11 Claims, 11 Drawing Sheets

(58) Field of Classification Search
CPC ............. G01N 35/00722; G01N 35/00; G01N 2035/0091; G01N 35/00623
See application file for complete search history.

(56) References Cited

U.S. PATENT DOCUMENTS

| | | | |
|---|---|---|---|
| 4,654,127 A | 3/1987 | Baker | |
| 4,887,455 A | 12/1989 | Payne et al. | |
| 5,034,506 A | 7/1991 | Summerton et al. | |
| 5,216,141 A | 6/1993 | Benner | |
| 5,235,033 A | 8/1993 | Summerton et al. | |
| 5,284,568 A | 2/1994 | Pace | |
| 5,320,808 A * | 6/1994 | Holen | B01L 3/508 |
| | | | 422/68.1 |
| 5,386,023 A | 1/1995 | Sanghvi et al. | |
| 5,591,578 A | 1/1997 | Meade et al. | |
| 5,602,240 A | 2/1997 | De Mesmaeker et al. | |
| 5,625,292 A | 4/1997 | Crook et al. | |
| 5,637,684 A | 6/1997 | Cook et al. | |
| 5,644,048 A | 7/1997 | Yau | |
| 5,681,702 A | 10/1997 | Collins et al. | |
| 5,705,348 A | 1/1998 | Meade et al. | |
| 5,770,365 A | 6/1998 | Lane et al. | |
| 5,781,024 A | 7/1998 | Blomberg et al. | |
| 5,807,701 A | 9/1998 | Payne et al. | |
| 5,824,473 A | 10/1998 | Meade et al. | |
| 5,837,546 A | 11/1998 | Allen | |
| 5,882,497 A | 3/1999 | Persaud et al. | |
| 5,968,329 A | 10/1999 | Anderson | |
| 6,013,170 A | 1/2000 | Meade | |
| 6,013,459 A | 1/2000 | Meade | |
| 6,023,961 A | 2/2000 | Discenzo | |
| 6,033,601 A | 3/2000 | Persaud et al. | |
| 6,063,573 A | 5/2000 | Kayyem | |
| 6,090,933 A | 7/2000 | Kayyem et al. | |
| 6,096,273 A | 8/2000 | Kayyem et al. | |
| 6,117,290 A | 9/2000 | Say | |
| 6,180,064 B1 | 1/2001 | Persaud et al. | |
| 6,190,858 B1 | 2/2001 | Persaud et al. | |
| 6,192,351 B1 | 2/2001 | Persaud | |
| 6,221,583 B1 | 4/2001 | Kayyem et al. | |
| 6,232,062 B1 | 5/2001 | Kayyem et al. | |
| 6,236,951 B1 | 5/2001 | Payne et al. | |
| 6,244,096 B1 | 6/2001 | Lewis et al. | |
| 6,248,229 B1 | 6/2001 | Meade | |
| 6,264,825 B1 | 7/2001 | Blackburn et al. | |
| 6,265,155 B1 | 7/2001 | Meade et al. | |
| 6,290,839 B1 | 9/2001 | Kayyem et al. | |
| 6,361,958 B1 | 3/2002 | Shieh et al. | |
| 6,376,232 B1 | 4/2002 | Payne et al. | |
| 6,387,707 B1 | 5/2002 | Seul et al. | |
| 6,431,016 B1 | 8/2002 | Payne | |
| 6,432,723 B1 | 8/2002 | Plaxco et al. | |
| 6,479,240 B1 | 11/2002 | Kayyem et al. | |
| 6,495,323 B1 | 12/2002 | Kayyem et al. | |
| 6,518,024 B2 | 2/2003 | Choong et al. | |
| 6,541,617 B1 | 4/2003 | Bamdad et al. | |
| 6,565,727 B1 | 5/2003 | Shenderov | |
| 6,596,483 B1 | 7/2003 | Choong et al. | |
| 6,600,026 B1 | 7/2003 | Yu | |
| 6,602,400 B1 | 8/2003 | Choong et al. | |
| 6,627,412 B1 | 9/2003 | Manning et al. | |
| 6,642,046 B1 | 11/2003 | McGarry et al. | |
| 6,655,010 B1 | 12/2003 | Hatfield et al. | |
| 6,661,434 B1 * | 12/2003 | MacPhail | G06F 3/0481 |
| | | | 715/846 |
| 6,673,533 B1 | 1/2004 | Wohlstadter et al. | |
| 6,686,150 B1 | 2/2004 | Blackburn et al. | |
| 6,740,518 B1 | 5/2004 | Duong et al. | |
| 6,753,143 B2 | 6/2004 | Tao et al. | |
| 6,761,816 B1 | 7/2004 | Blackburn et al. | |
| 6,773,566 B2 | 8/2004 | Shenderov | |
| 6,824,669 B1 | 11/2004 | Li et al. | |
| 6,833,267 B1 | 12/2004 | Kayyem | |
| 6,875,619 B2 | 4/2005 | Blackburn | |
| 6,942,771 B1 | 9/2005 | Kayyem | |
| 6,951,759 B2 | 10/2005 | Travers et al. | |
| 6,960,467 B2 | 11/2005 | Shieh et al. | |
| 6,977,151 B2 | 12/2005 | Kayyem et al. | |
| 7,014,992 B1 | 3/2006 | Kayyem et al. | |
| 7,018,523 B2 | 3/2006 | Meade | |
| 7,045,285 B1 | 5/2006 | Kayyem et al. | |
| 7,056,669 B2 | 6/2006 | Kayyem et al. | |
| 7,087,148 B1 | 8/2006 | Blackburn et al. | |
| 7,090,804 B2 | 8/2006 | Kayyem et al. | |
| 7,125,668 B2 | 10/2006 | Kayyem et al. | |
| 7,160,678 B1 | 1/2007 | Kayyem et al. | |
| 7,172,897 B2 | 2/2007 | Blackburn et al. | |
| 7,255,780 B2 | 8/2007 | Shenderov | |
| 7,267,939 B2 | 9/2007 | Meade | |
| 7,312,087 B2 | 12/2007 | Duong et al. | |
| 7,381,525 B1 | 6/2008 | Kayyem et al. | |
| 7,381,533 B2 | 6/2008 | Kayyem et al. | |
| 7,384,749 B2 | 6/2008 | Kayyem et al. | |
| 7,393,645 B2 | 7/2008 | Kayyem et al. | |
| 7,439,014 B1 | 10/2008 | Pamula et al. | |
| 7,514,228 B2 | 4/2009 | Meade | |
| 7,534,331 B2 | 5/2009 | Kayyem | |
| 7,560,237 B2 | 7/2009 | O'Connor et al. | |
| 7,566,534 B2 | 7/2009 | Meade | |
| 7,579,145 B2 | 8/2009 | Meade | |
| 7,582,419 B2 | 9/2009 | Meade | |
| 7,595,153 B2 | 9/2009 | Meade | |
| 7,601,507 B2 | 10/2009 | O'Connor et al. | |
| 7,655,129 B2 | 2/2010 | Blackburn et al. | |
| 7,713,711 B2 | 5/2010 | O'Connor et al. | |
| 7,727,723 B2 | 6/2010 | Pollack et al. | |
| 7,759,073 B2 | 7/2010 | O'Connor et al. | |
| 7,763,471 B2 | 7/2010 | Pamula et al. | |
| 7,815,871 B2 | 10/2010 | Pamula et al. | |
| 7,816,121 B2 | 10/2010 | Pollack et al. | |
| 7,820,391 B2 | 10/2010 | Chunlin | |
| 7,822,510 B2 | 10/2010 | Paik et al. | |
| 7,851,184 B2 | 12/2010 | Pollack et al. | |
| 7,863,035 B2 | 1/2011 | Clemens et al. | |
| 7,901,947 B2 | 3/2011 | Pollack et al. | |
| 7,919,330 B2 | 4/2011 | de Guzman et al. | |
| 7,935,481 B1 | 5/2011 | Umek et al. | |
| 7,939,021 B2 | 5/2011 | Smith et al. | |
| 7,943,030 B2 | 5/2011 | Shenderov | |
| 7,998,436 B2 | 8/2011 | Pollack et al. | |
| 8,007,739 B2 | 8/2011 | Pollack et al. | |
| 8,012,743 B2 | 9/2011 | Bamdad et al. | |
| 8,041,463 B2 | 10/2011 | Pollack et al. | |
| 8,048,628 B2 | 11/2011 | Pollack et al. | |
| 8,088,578 B2 | 1/2012 | Hua et al. | |
| 8,093,062 B2 | 1/2012 | Winger | |
| 8,114,661 B2 | 2/2012 | O'Connor et al. | |
| 8,137,917 B2 | 3/2012 | Pollack et al. | |
| 8,202,686 B2 | 6/2012 | Pamula et al. | |
| 8,208,146 B2 | 6/2012 | Srinivasan et al. | |
| 8,268,246 B2 | 9/2012 | Srinivasan et al. | |
| D669,191 S | 10/2012 | Handique | |
| 8,304,253 B2 | 11/2012 | Yi et al. | |
| 8,313,698 B2 | 11/2012 | Pollack et al. | |
| 8,313,895 B2 | 11/2012 | Pollack et al. | |
| 8,317,990 B2 | 11/2012 | Pamula et al. | |
| 8,349,276 B2 | 1/2013 | Pamula et al. | |
| 8,364,315 B2 | 1/2013 | Sturmer et al. | |
| 8,388,909 B2 | 3/2013 | Pollack et al. | |
| 8,389,297 B2 | 3/2013 | Pamula et al. | |
| 8,394,641 B2 | 3/2013 | Winger | |
| 8,426,213 B2 | 4/2013 | Eckhardt et al. | |
| 8,440,392 B2 | 5/2013 | Pamula et al. | |
| 8,454,905 B2 | 6/2013 | Pope et al. | |
| 8,460,528 B2 | 6/2013 | Pollack et al. | |
| 8,470,606 B2 | 6/2013 | Srinivasan et al. | |
| 8,481,125 B2 | 7/2013 | Yi et al. | |
| 8,492,168 B2 | 7/2013 | Srinivasan et al. | |
| 8,541,176 B2 | 9/2013 | Pamula et al. | |
| 8,541,177 B2 | 9/2013 | Chan | |
| 8,614,087 B2 | 12/2013 | Drader | |
| 8,709,787 B2 | 4/2014 | Handique | |
| 9,132,423 B2 | 9/2015 | Battrell et al. | |

(56)　　　　References Cited

U.S. PATENT DOCUMENTS

| | | |
|---|---|---|
| 9,222,623 B2 | 12/2015 | Wright et al. |
| 9,254,489 B2 | 2/2016 | Lin et al. |
| 9,498,778 B2 | 11/2016 | Corey et al. |
| 9,598,722 B2 | 3/2017 | Wright et al. |
| 9,601,879 B1 | 3/2017 | Lin et al. |
| 9,957,553 B2 | 5/2018 | Kayyem et al. |
| 10,184,884 B2 | 1/2019 | Anderson et al. |
| 10,352,983 B1 | 7/2019 | Taylor |
| 10,564,211 B1 | 2/2020 | Taylor |
| 10,753,986 B2 | 8/2020 | Taylor et al. |
| 11,300,578 B2 | 4/2022 | Nguyen et al. |
| 11,391,790 B2 | 7/2022 | Taylor et al. |
| 11,635,475 B2 | 4/2023 | Taylor |
| 2002/0107647 A1 | 8/2002 | Anderson et al. |
| 2002/0137238 A1 | 9/2002 | Mockel et al. |
| 2004/0009607 A1 | 1/2004 | Goodman |
| 2004/0024051 A1 | 2/2004 | Holton |
| 2004/0101191 A1 | 5/2004 | Seul et al. |
| 2004/0189311 A1 | 9/2004 | Glezer et al. |
| 2005/0136552 A1 | 6/2005 | Buechler |
| 2006/0192015 A1 | 8/2006 | DiGiovanna |
| 2007/0143313 A1 | 6/2007 | Cotner |
| 2007/0241068 A1 | 10/2007 | Pamula et al. |
| 2007/0242105 A1 | 10/2007 | Srinivasan et al. |
| 2007/0275415 A1 | 11/2007 | Srinivasan et al. |
| 2008/0230386 A1 | 9/2008 | Srinivasan et al. |
| 2008/0274513 A1 | 11/2008 | Shenderov et al. |
| 2009/0117571 A1 | 5/2009 | Solanki |
| 2009/0155902 A1 | 6/2009 | Pollack et al. |
| 2009/0202390 A1 | 8/2009 | Iizumi et al. |
| 2009/0263834 A1 | 10/2009 | Sista et al. |
| 2009/0304944 A1 | 12/2009 | Sudarsan et al. |
| 2010/0010602 A1 | 1/2010 | Wedan et al. |
| 2010/0025250 A1 | 2/2010 | Pamula et al. |
| 2010/0028984 A1 | 2/2010 | Duong et al. |
| 2010/0032293 A1 | 2/2010 | Pollack et al. |
| 2010/0048410 A1 | 2/2010 | Shenderov et al. |
| 2010/0068764 A1 | 3/2010 | Sista et al. |
| 2010/0084270 A1 | 4/2010 | Vulto |
| 2010/0087012 A1 | 4/2010 | Shenderov |
| 2010/0106206 A1 | 4/2010 | Aghassian et al. |
| 2010/0116640 A1 | 5/2010 | Pamula et al. |
| 2010/0120130 A1 | 5/2010 | Srinivasan et al. |
| 2010/0130369 A1 | 5/2010 | Shenderov et al. |
| 2010/0190263 A1 | 7/2010 | Srinivasan et al. |
| 2010/0194408 A1 | 8/2010 | Sturmer et al. |
| 2010/0206094 A1 | 8/2010 | Shenderov |
| 2010/0236928 A1 | 9/2010 | Srinivasan et al. |
| 2010/0236929 A1 | 9/2010 | Pollack et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0291578 A1 | 11/2010 | Pollack et al. |
| 2010/0307917 A1 | 12/2010 | Srinivasan et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0160808 A1 | 6/2011 | Lyden et al. |
| 2011/0180571 A1 | 7/2011 | Srinivasan et al. |
| 2011/0186433 A1 | 8/2011 | Pollack et al. |
| 2011/0201099 A1 | 8/2011 | Anderson |
| 2011/0203930 A1 | 8/2011 | Pamula et al. |
| 2011/0209998 A1 | 9/2011 | Shenderov |
| 2011/0269239 A1 | 11/2011 | Diessel et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0038477 A1 | 2/2012 | Torgerson et al. |
| 2012/0044299 A1 | 2/2012 | Winger |
| 2012/0132528 A1 | 5/2012 | Shenderov et al. |
| 2012/0165238 A1 | 6/2012 | Pamula et al. |
| 2012/0178091 A1 | 7/2012 | Glezer et al. |
| 2012/0181186 A1 | 7/2012 | Bertin et al. |
| 2012/0182562 A1 | 7/2012 | Yang et al. |
| 2012/0261264 A1 | 10/2012 | Srinivasan et al. |
| 2012/0282602 A1 | 11/2012 | Drader et al. |
| 2013/0017544 A1 | 1/2013 | Eckhardt et al. |
| 2013/0018611 A1 | 1/2013 | Sturmer |
| 2013/0053666 A1 | 2/2013 | Hughes et al. |
| 2013/0059366 A1 | 3/2013 | Pollack et al. |
| 2013/0118901 A1 | 5/2013 | Pollack et al. |
| 2013/0130369 A1 | 5/2013 | Wilson et al. |
| 2013/0130936 A1 | 5/2013 | Eckhardt |
| 2013/0146461 A1 | 6/2013 | Pamula et al. |
| 2013/0164742 A1 | 6/2013 | Pollack et al. |
| 2013/0178374 A1 | 7/2013 | Eckhardt et al. |
| 2013/0178968 A1 | 7/2013 | Sturmer et al. |
| 2013/0203606 A1 | 8/2013 | Pollack et al. |
| 2013/0217103 A1 | 8/2013 | Bauer |
| 2013/0217113 A1 | 8/2013 | Srinivasan et al. |
| 2013/0225450 A1 | 8/2013 | Pollack et al. |
| 2013/0225452 A1 | 8/2013 | Pollack et al. |
| 2013/0230875 A1 | 9/2013 | Pamula et al. |
| 2013/0233425 A1 | 9/2013 | Srinivasan et al. |
| 2013/0233712 A1 | 9/2013 | Pamula et al. |
| 2013/0252262 A1 | 9/2013 | Srinivasan et al. |
| 2013/0257625 A1 | 10/2013 | Holle |
| 2014/0125352 A1 | 5/2014 | Franke et al. |
| 2014/0154792 A1 | 6/2014 | Moynihan et al. |
| 2014/0170735 A1 | 6/2014 | Holmes et al. |
| 2014/0194305 A1 | 7/2014 | Kayyem et al. |
| 2014/0252079 A1 | 9/2014 | Bjerke et al. |
| 2014/0273187 A1 | 9/2014 | Johnson et al. |
| 2014/0322706 A1 | 10/2014 | Kayyem et al. |
| 2014/0336083 A1 | 11/2014 | Khattak et al. |
| 2014/0370609 A1 | 12/2014 | Frank et al. |
| 2015/0087559 A1 | 3/2015 | Putnam et al. |
| 2015/0184235 A1 | 7/2015 | Reda |
| 2015/0323555 A1 | 11/2015 | Kayyem et al. |
| 2015/0331037 A1 | 11/2015 | Liu et al. |
| 2015/0340718 A1* | 11/2015 | Barton ..................... C01B 3/02 422/114 |
| 2016/0097764 A1 | 4/2016 | Taslim et al. |
| 2016/0129437 A1 | 5/2016 | Kayyem et al. |
| 2016/0129445 A1 | 5/2016 | Corey et al. |
| 2016/0130640 A1 | 5/2016 | Wright et al. |
| 2016/0142407 A1* | 5/2016 | Chun .................. H04L 63/0861 726/5 |
| 2016/0169578 A1 | 6/2016 | Linney, II |
| 2016/0169956 A1 | 6/2016 | Kim |
| 2016/0209837 A1 | 7/2016 | Kim |
| 2017/0036210 A1 | 2/2017 | Corey et al. |
| 2018/0095054 A1 | 4/2018 | Huo et al. |
| 2018/0095100 A1* | 4/2018 | Nguyen ............. B01L 3/50273 |
| 2018/0126381 A1 | 5/2018 | Huff et al. |
| 2019/0003929 A1 | 1/2019 | Shapiro et al. |
| 2019/0232279 A1 | 8/2019 | Jensen et al. |
| 2020/0101279 A1* | 4/2020 | Drake ................ A61N 1/37205 |
| 2020/0110123 A1* | 4/2020 | Taylor ................... G01R 31/68 |
| 2020/0379058 A1 | 12/2020 | Taylor et al. |
| 2022/0365146 A1 | 11/2022 | Taylor et al. |

FOREIGN PATENT DOCUMENTS

| | | |
|---|---|---|
| EP | 0222612 A2 | 5/1987 |
| JP | 201456575 A | 3/2014 |
| WO | 1999037819 A2 | 7/1999 |
| WO | 2004027549 A2 | 4/2004 |
| WO | 2015191916 A1 | 12/2015 |
| WO | 2018053501 A1 | 3/2018 |
| WO | 2018168432 A1 | 9/2018 |

OTHER PUBLICATIONS

Liang, Stephen et al., Empiric Antimicrobial Therapy in Severe Sepsis and Septic Shock: Optimizing Pathogen Clearance, Curr Infect Dis Rep., Jul. 2015, 17(7): 493.

(56) References Cited

OTHER PUBLICATIONS

EP: Examination Report issued in European Patent Application No. 17781237.7 dated Oct. 27, 2021.
EP: Supplementary Search Report dated Mar. 25, 2022 in European Patent Application No. 19869371.5.
Locharla et al., "Variable length mixed radix MDC FFT/IFFT processor for MIMO-OFDM application" IET Comput. Digit. Tech., 12(1) 9-19 (2018).
Sipherd, "The third-leading cause of death in US most doctors don't want you to know about" CNBC: Modern Medicine, Feb. 22, 2018, available at https://www.cnbc.com/2018/02/22/medical-errors-third-leading-cause-of-death-in-america.html.
US: Final Office Action dated Oct. 5, 2021 in U.S. Appl. No. 15/708,847.
US: Non-Final Office Action dated Jun. 15, 2021 in U.S. Appl. No. 15/708,847.
WO: International Preliminary Report on Patentability PCT/US2021/037051 Dec. 13, 2022) 8pp.
WO: International Search Report and Written Opinion dated Dec. 11, 2017 in PCT/US2017/052248.
EP: Extended European Search Report issued in EP Patent Application No. 21822120.8 dated May 14, 2024 (12 pages).
JP: Office Action (Japanese language) issued in Japanese Patent Application No. 2022-575991, 6 pages (dated May 23, 2025). Concise Explanation of Relevance attached.

* cited by examiner

User Interface  125

| Gray | Purple |
|---|---|
| Gray | Purple |
| Purple | Purple |
| Muted Orange | Muted Orange |
| Gray | Gray |

*FIG. 3*

Software Architecture  26

| Disable bay monitoring | Standby bay monitoring | Suggest bay monitoring |

SYSTEMS AND METHODS FOR ASSESSING BAYS ON DIAGNOSTIC DEVICES

CROSS-REFERENCE TO RELATED APPLICATIONS

This application is a U.S. national phase application under 35 U.S.C. § 371 of PCT/US2021/037051, filed on Jun. 11, 2021 and entitled "SYSTEMS AND METHODS FOR ASSESSING BAYS ON DIAGNOSTIC DEVICES," which claims the benefit of U.S. Provisional Application No. 63/038,613, titled "SYSTEMS AND METHODS FOR ASSESSING BAYS ON DIAGNOSTIC DEVICES," filed on Jun. 12, 2020." The entire content of the aforementioned patent applications are incorporated by reference as part of the disclosure of this patent document for all purposes.

TECHNICAL FIELD

The present technology relates to monitoring diagnostic instruments to improve field validity rates.

BACKGROUND

Preventable medical errors are now the third leading cause of death in the United States at more than 250,000 deaths per year. Some rapid molecular diagnostic systems, like GenMark's ePlex system, are designed to reduce medical error. Yet, no matter how well a diagnostic system is designed, diagnostic instruments wear over time. If a diagnostic instrument is not performing properly, preventable medical errors can occur. If the instrument cannot be used, the laboratory cannot process samples. In some cases, failure to process samples can be deadly, such as for sample processing cartridges which detect organisms that cause sepsis. Recent studies have shown that patients with severe sepsis or septic shock face a 7.6% increased likelihood of death for every hour in which antibiotic therapy is not applied. Liang et al., *Empiric Antimicrobial Therapy in Severe Sepsis and Septic Shock: Optimizing Pathogen Clearance*, Curr Infect Dis Rep. 2015 July; 17(7): 493. Further, when a laboratory cannot process samples, cartridges may expire. Consistently supplying laboratories and hospitals with cartridges for processing patient samples is difficult because of the cartridges' short shelf-life and the seasonal demand for some tests. For example, during the most devastating period of the coronavirus pandemic in 2019 and 2020, many hospitals/laboratories were at critically low levels of rapid molecular respiratory cartridges.

SUMMARY

Provided herein in certain embodiments, methods, systems and tools for improving field validity rates of diagnostic instruments.

In some embodiments in accordance with the present technology, a diagnostic instrument includes (a) a bay; (b) a control unit, where the control unit comprises a disable bay rule engine, a standby rule engine and a suggest rule engine, wherein the disable bay monitoring rule engine produces disable bay data, the standby monitoring rule engine produces standby bay data and the suggest monitoring rule engine produces suggest bay data; and (c) a processor, wherein the processor determines whether the disable bay data, the standby bay data and the suggest bay data meet a predefined baseline; and in response to determining that the disable bay data does not meet the predefined baseline, the processor disables the bay.

BRIEF DESCRIPTION OF THE DRAWINGS

FIG. 3 is a block diagram of a user interface in accordance with the principles of the present technology.

FIG. 5 is a block diagram of the software architecture in accordance with the principles of the present technology.

FIG. 8 is a representative diagnostic instrument showing how the bay icons correspond to the bays in the processing instrument.

DETAILED DESCRIPTION

Figure 1:
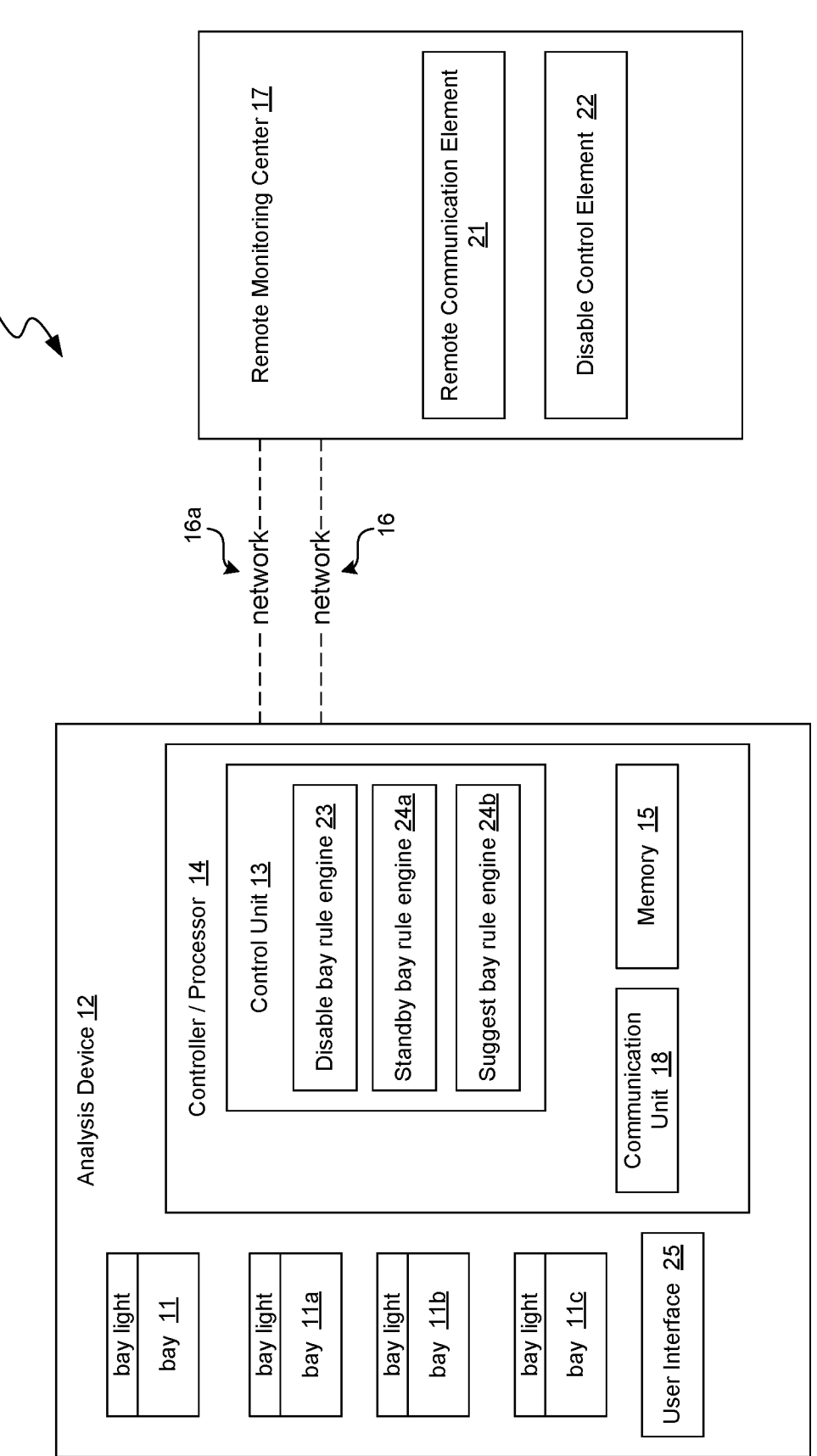
FIG. 1 is a block diagram of a diagnostic instrument in accordance with the principles of the present technology.

The following description of the present technology is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

In accordance with various embodiments of the present technology, a system, device and method are provided for location-based diagnostic instruments, e.g., the instrument is located at the client's location. Accordingly, the system, device and method components have been represented where appropriate by convention symbols in the drawings, e.g., showing specific details that are pertinent to understanding the embodiments of the invention so as not to obscure the disclosure with details that will be readily apparent to those of ordinary skill in the art having the benefit of the description herein. While the invention is described herein with respect to a diagnostic system, the invention is not limited to such. It is contemplated that the processes and functions described herein may be applied to any instrument with processing compartments and in particular to instruments with processing compartments that are randomly and independently addressable.

As used herein, relational terms, such as "first" and "second," "top" and "bottom," and the like, may be used solely to distinguish one entity or element from another entity or element without necessarily requiring or implying any physical or logical relationship or order between such entities or elements.

Generally, the present disclosure relates to methods, systems and tools for improving field validity rates of diagnostic instruments.

High throughput diagnostic instruments can process multiple samples simultaneously. Each sample is processed in its own processing bay (also referred to as a bay or a processing unit). Many diagnostic instruments have what is called "random and continuous access." This means that a sample can be loaded into any processing bay in any order. For example, the first sample processed need not go into the first bay; it can go into any available bay. In practice, even though bays are "randomly accessible," technicians tend to use the same bays over and over again. In particular, the bay in the top-left corner is used first and then bays further down the column are used. For example, a top-left bay may get used twice as often as a bottom-right bay because of user preference. This makes some bays wear out faster, require maintenance sooner, etc. By suggesting bays, disabling bays or putting some bays on standby, the instrument can drive more even usage of instrument bays. This will reduce the number of service calls needed, extend the lifetime of a bay and instrument, and improve user satisfaction.

Additionally, some bays in the field empirically operate better than others, i.e., have better validity rates, have fewer run errors, connect better to sample cartridges, etc. Therefore, it is desirable to drive users to bays that operate better than others. Or, stated another way, drive users away from bays that operate more poorly than others. This can be achieved by disabling bays that are not performing as well as they should. This can also be achieved by suggesting a high performing bay to a user. Bays of adequate performance can be put on standby, i.e., not suggested, until all of the high performing, suggested bays are in use. In this way, validity rates in the field will improve: bad bays are turned off good bays are used over failing bays; good bays are used over degrading bays.

Existing diagnostic instruments only generate system alerts, i.e., they generate alerts when the whole system is malfunctioning. But there is no mechanism in place to turn off only a portion of a system, suggest using the "best" portion of the system, put a portion of the system on standby for later use if needed, or combinations thereof. The technology disclosed herein addresses and resolves these and other technical problems and shortcomings with existing diagnostic instruments.

In some embodiments of the disclosed methods, systems, devices, and computer-programmable products, the following techniques can be implemented. For example, after a sample cartridge is processed in a bay of a diagnostic instrument, the instrument begins an analysis to determine whether the bay should be disabled. The instrument processor compares the particular bay's run data to historical data in the disable bay rule engine. If the bay does not meet the minimum disable bay threshold data, the bay is disabled and the graphical user interface (GUI) is modified. The disable bay data can be, but is not limited to, if the bay experienced four or more invalid runs out of the last ten samples processed, the bay is disabled. In some embodiments, when a bay is disabled the GUI is modified so that the bay icon corresponding to the bay used is grayed out on the user interface, visually indicating to the user that it is disabled. In some embodiments, when a bay is disabled the bay light is modified (grayed out) visually, indicating to the user that it is disabled.

In some embodiments, for example, after a sample cartridge is processed in a bay, the instrument begins an analysis to determine whether the bay should be disabled, suggested, or put on standby. The instrument processor begins by comparing the particular bay's run data to historical disable bay threshold data in the disable bay rule engine. If the bay does not meet the minimum disable bay threshold data, the bay is disabled and the GUI is modified. If the bay meets the minimum disable bay threshold data, the processor then reviews standby bay data. The instrument processor then compares the particular bay's run data to historical standby bay threshold data in the standby rule engine. If the bay does not meet the standby bay threshold data, the bay is put on standby and the GUI is modified. The standby bay data can be, but is not limited to, if the bay experienced one to three invalid runs out of the last ten samples processed, the bay is put on standby. When a bay is put on standby, the GUI is modified so that the bay icon corresponding to the bay used is not suggested on the user interface, visually indicating to the user that it is not a suggested bay but is still available for use. In some embodiments, when a bay is on standby the GUI is modified so that the bay icon corresponding to the bay used is muted orange, visually indicating to the user that it is on standby.

In some embodiments, for example, if the bay run data meets the minimum disable bay data, the bay is suggested and the GUI is modified. When a bay is suggested the GUI is modified so that the bay icon corresponding to the bay used is lit up on the user interface, visually indicating to the user that it is a suggested bay. In some embodiments, when a bay is suggested the GUI is modified so that the bay icon corresponding to the bay used is purple, visually indicating to the user that it is suggested.

In some embodiments, for example, if the bay run data meets the minimum standby bay data, the bay is suggested and the GUI is modified. When a bay is suggested the GUI is modified so that the bay icon corresponding to the bay used is lit up on the user interface, visually indicating to the user that it is a suggested bay. In some embodiments, when a bay is suggested the GUI is modified so that the bay icon corresponding to the bay used is purple, visually indicating to the user that the corresponding bay is suggested.

In some embodiments, for example, if the bay run data meets the minimum disable bay data and minimum standby bay data, the processor then analyzes the data in the suggest bay rule engine. The instrument processor compares the particular bay's run data to historical suggest bay threshold data. In an embodiment, if the bay meets the minimum suggest bay threshold data, the bay is suggested and the GUI is modified. When a bay is suggested the GUI is modified so that the bay icon corresponding to the bay used is lit up on the user interface, visually indicating to the user that it is a suggested bay. In some embodiments, when a bay is suggested the GUI is modified so that the bay icon corresponding to the bay used is purple, visually indicating to the user that it is suggested.

Figure 10:
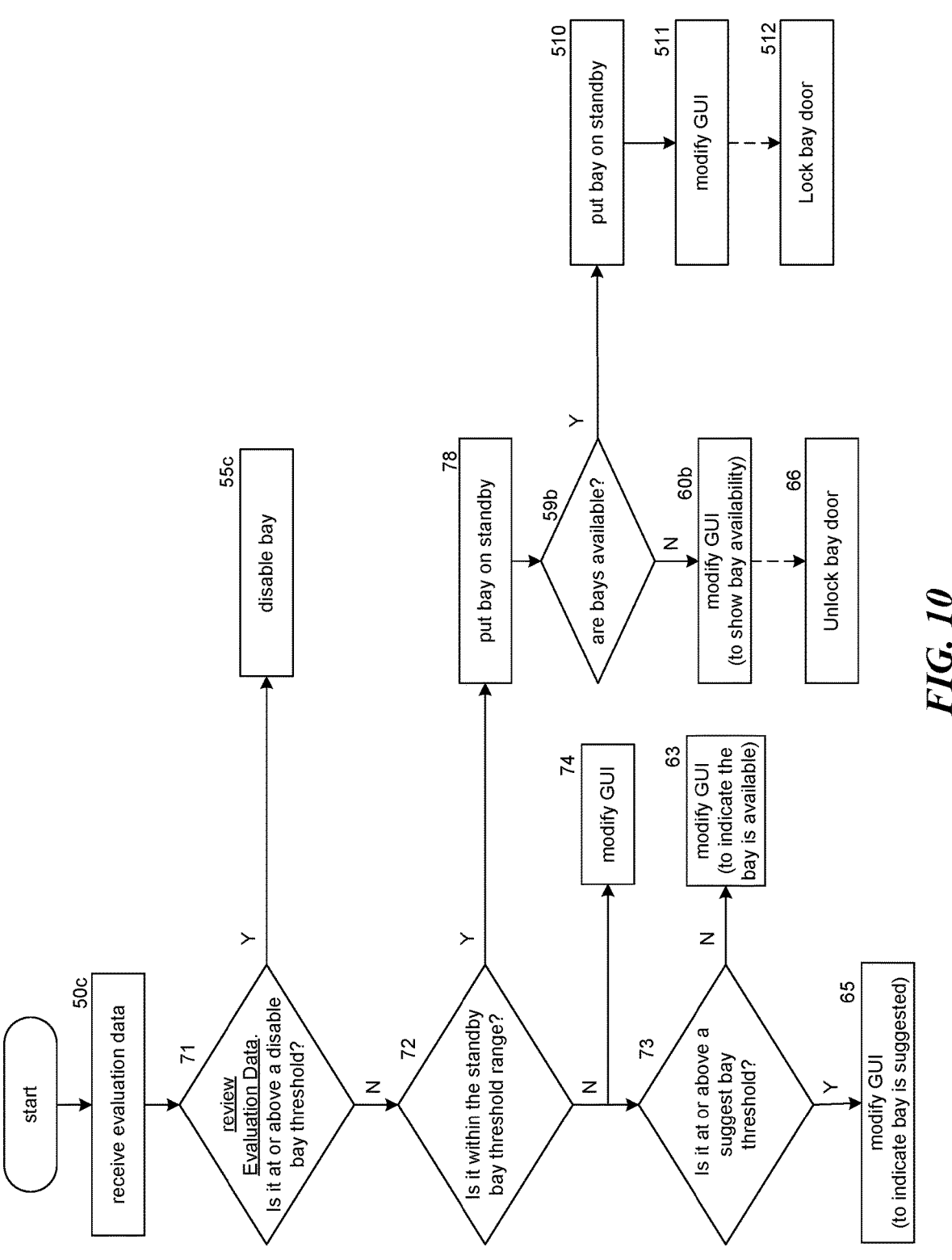
FIG. 10 is a flow chart of an evaluate bay monitoring procedure in accordance with the principles of the present technology.

In some embodiments, for example, multiple data sets are evaluated by multiple rule engines. In an embodiment, a single data set (evaluation data) is evaluated by multiple rule engines (FIG. 10). Each rule engine has its own thresholds for disabling the bay, putting the bay on standby and/or suggesting a bay. The instrument processor compares the particular bay's run data to historical threshold data in each rule engine. In an embodiment, if the bay meets the minimum suggest bay threshold data, the bay is suggested and the GUI is modified, or, if the bay meets the minimum disable bay threshold data, the bay is disabled and the GUI is modified, or, if the bay meets the minimum standby bay threshold data (or range), the bay is put on standby and the GUI is modified.

Figure 11:
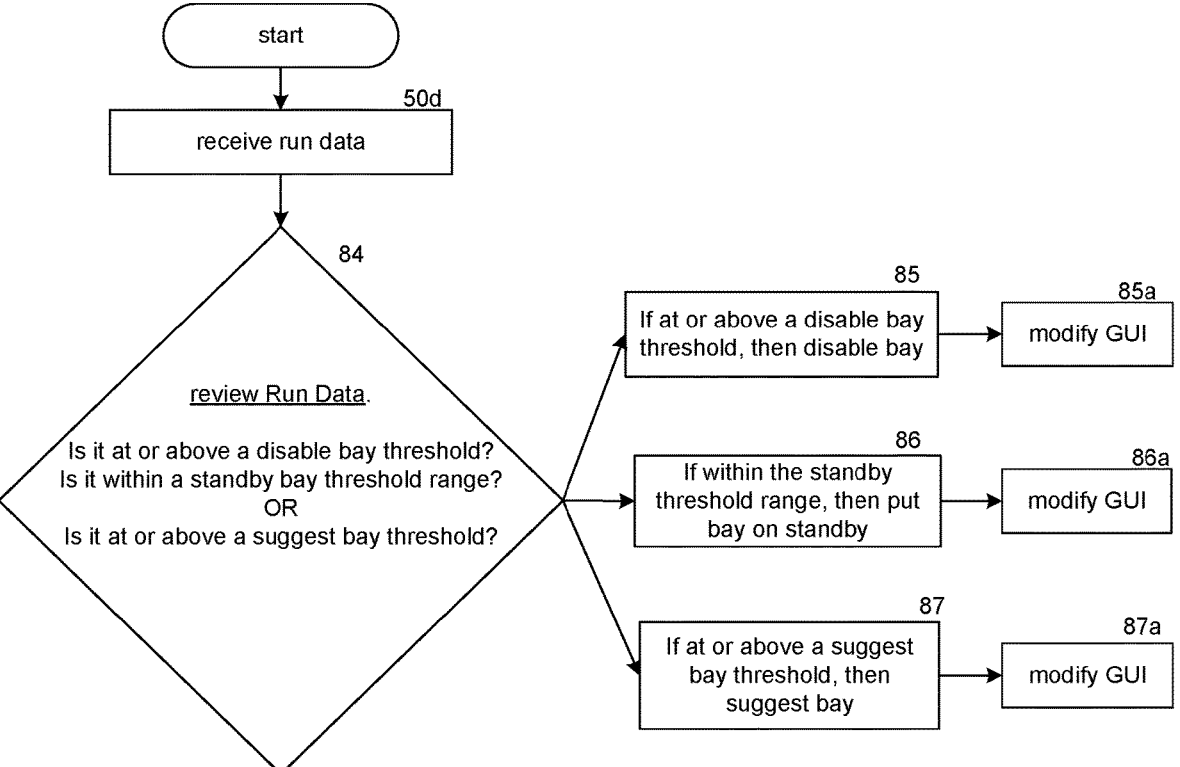
FIG. 11 is a flow chart of an assess bay monitoring procedure in accordance with the principles of the present technology.

In some embodiments, for example, the bay run data is evaluated by a single rule engine (sometimes referred to as an assess rule engine) (FIG. 11). The rule engine has thresholds for disabling the bay, putting the bay on standby and/or suggesting a bay. The instrument processor compares the particular bay's run data to historical threshold data on the rule engine. In an embodiment, if the bay meets the minimum suggest bay threshold data, the bay is suggested and the GUI is modified, or, if the bay meets the minimum disable bay threshold data, the bay is disabled and the GUI is modified, or, if the bay meets the minimum standby bay threshold data (or range), the bay is put on standby and the GUI is modified.

In some embodiments, for example, the diagnostic instrument is connected to a remote controller. In this situation, the remote controller (not the instrument) performs the disable bay analysis, standby bay analysis and suggest bay analysis (collectively referred to as bay data analysis).

In some embodiments, for example, the bay monitoring will disable, put bays on standby and/or suggest bays automatically. In some embodiments, users are automatically notified and will be prompted to contact Technical Support for further investigation. An option to override the bay disable, standby and/or suggest features is available.

The invention can be realized in hardware, software, or a combination of hardware and software. Any kind of computing system, or other apparatus adapted for carrying out the methods described herein, is suited to perform the functions described herein. A typical combination of hardware and software could be a specialized or general purpose computer system having one or more processing elements and a computer program stored on a storage medium that, when loaded and executed, controls the computer system such that it carries out the methods described herein. The invention can also be embedded in a computer program product, which comprises all the features enabling the implementation of the methods described herein, and which, when loaded in a computing system, is able to carry out these methods. Storage medium refers to any volatile or nonvolatile storage device.

Computer program or application in the present context means any expression, in any language, code or notation, of a set of instructions intended to cause a system having an information processing capability to perform a particular function either directly or after either or both of the following: a) conversion to another language, code or notation; b) reproduction in a different material form.

It will be appreciated by persons skilled in the art that the invention is not limited to what has been particularly shown and described hereinabove. In addition, unless mention was made above to the contrary, it should be noted that all of the accompanying drawings are not to scale. A variety of modifications and variations are possible in light of the above teachings without departing from the scope and spirit of the invention.

It is understood that, while several example embodiments describe comparison of data to be "below," "at or below," "above," "at or above," or "at" a threshold value and/or threshold range, the disclosed methods, systems, devices, and computer products are not limited to any particular example comparison.

Herein, "bay run data" and "bay data" may be used interchangeably. Also, "bay data" or "bay run data" may be referred to as "standby bay data" when used in the context of evaluating whether the bay should be put on standby, or as "suggest bay data" when used in the context of suggestion (e.g., suggest which bay to use next), or as "disable bay data" when used in the context of evaluating whether the bay should be disabled. Evaluate data, disable bay data, standby bay data, and suggest bay data can be based on how the processing unit functions, how the diagnostic instrument functions, how the diagnostic assay functions, behavioral characteristics or combinations thereof.

The evaluate data, disable bay data, standby bay data and suggest bay data can be, but are not limited to, the factors set forth in Table 1.

Diagnostic Instrument

In reference to the drawings, like reference designators refer to like elements.

FIG. 1 is a block diagram of a diagnostic instrument in accordance with the principles of the present technology. The diagnostic instrument of FIG. 1 illustrates example embodiments of a location-based self-monitoring system constructed in accordance with the principles of the invention and designated generally as "10". System 10 may include an analysis device 12, also referred to as location device 12, in which the location device may comprise a base station comprising: (i) one or more processing compartments referred to as bays 11*a* to 11*n* (collectively referred to as "cartridge processing bays" or "bays" 11), (ii) a user interface 25 (e.g., graphical user interface) comprising a touch screen display having a plurality of bay icons, each icon uniquely corresponding to one of said plurality of bays, (iii) a processor 14 (also referred to as controller/processor), the processor 14 may comprise control unit 13, a memory 15, and a communication rule engine 18 (also referred to as a communication unit). The sample-to-answer system is generally described in U.S. Pat. Nos. 9,957,553, 9,598,722 and U.S.

Figure 8:
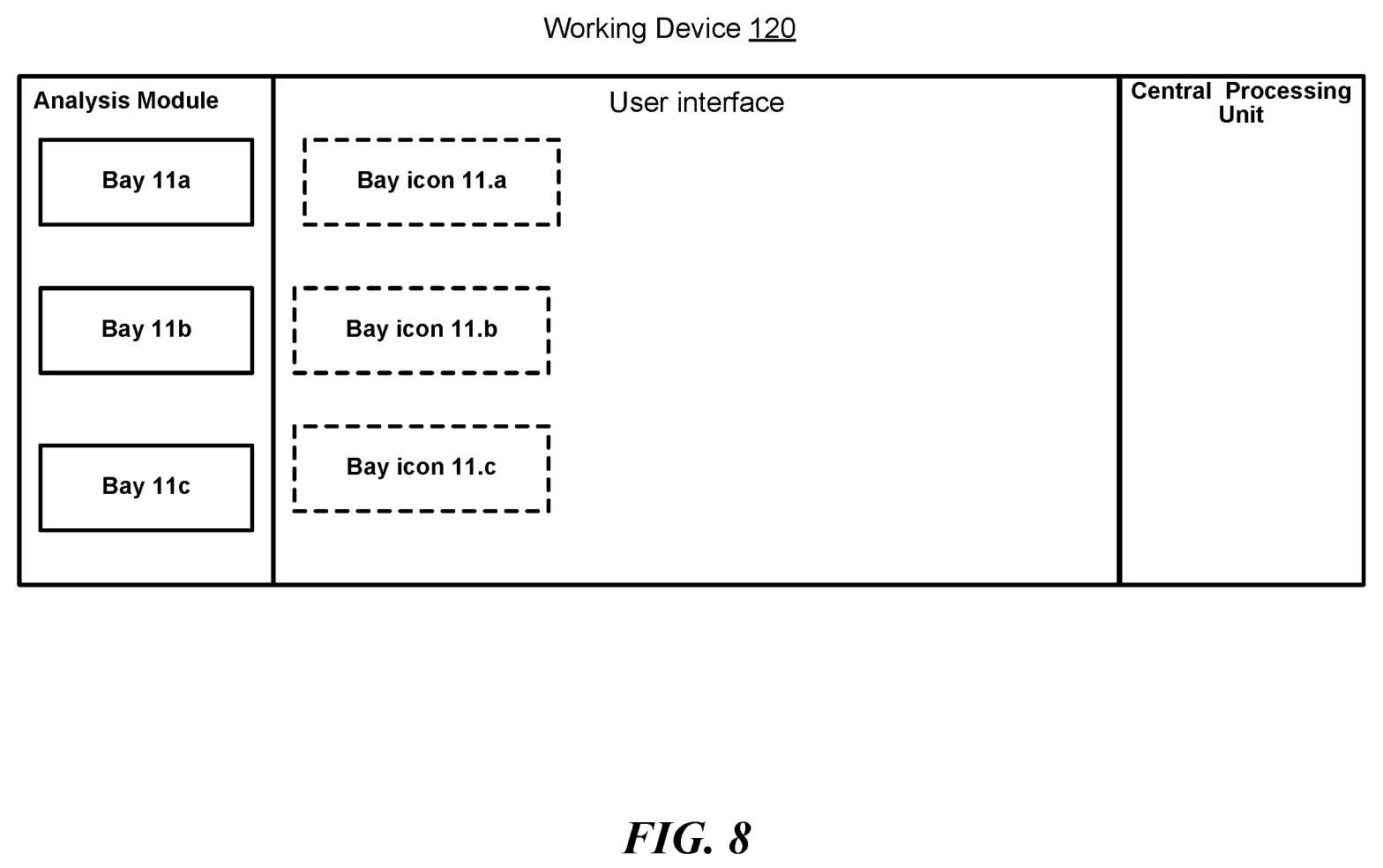

Patent Publication no. 2018/0095100, all of which are incorporated by reference in their entirety. FIG. 8 shows how the bay icons correspond to the bays in the processing instrument, as an example.

FIG. 8 shows a diagram illustrating an example embodiment of a diagnostic instrument, shown as "working device 120". The diagram of the example diagnostic instrument shows how the bay icons 11.*a*, 11.*b*, and 11.*c* of a user interface of the working device 120 correspond to the bays 11*a*, 11*b*, and 11*c* in an analysis module of the working device 120, respectively. The working device 120 includes a processing unit coupled to the analysis module and the user interface.

Each processing bay is configured to receive a cartridge and process the cartridge independently of the other bays. This is referred to as "random and continuous access," meaning any available bay can be used at any time; the bays need not be used or loaded in any particular order.

In some embodiments, the location device 12 is connected to one or more networks 16*a* to 16*n* (collectively referred to as "network 16") and one or more remote monitoring centers 17*a* to 17*n* (collectively referred to as "remote monitoring center 17"). In some embodiments, the remote monitoring centers may communicate with each other.

Figure 2:
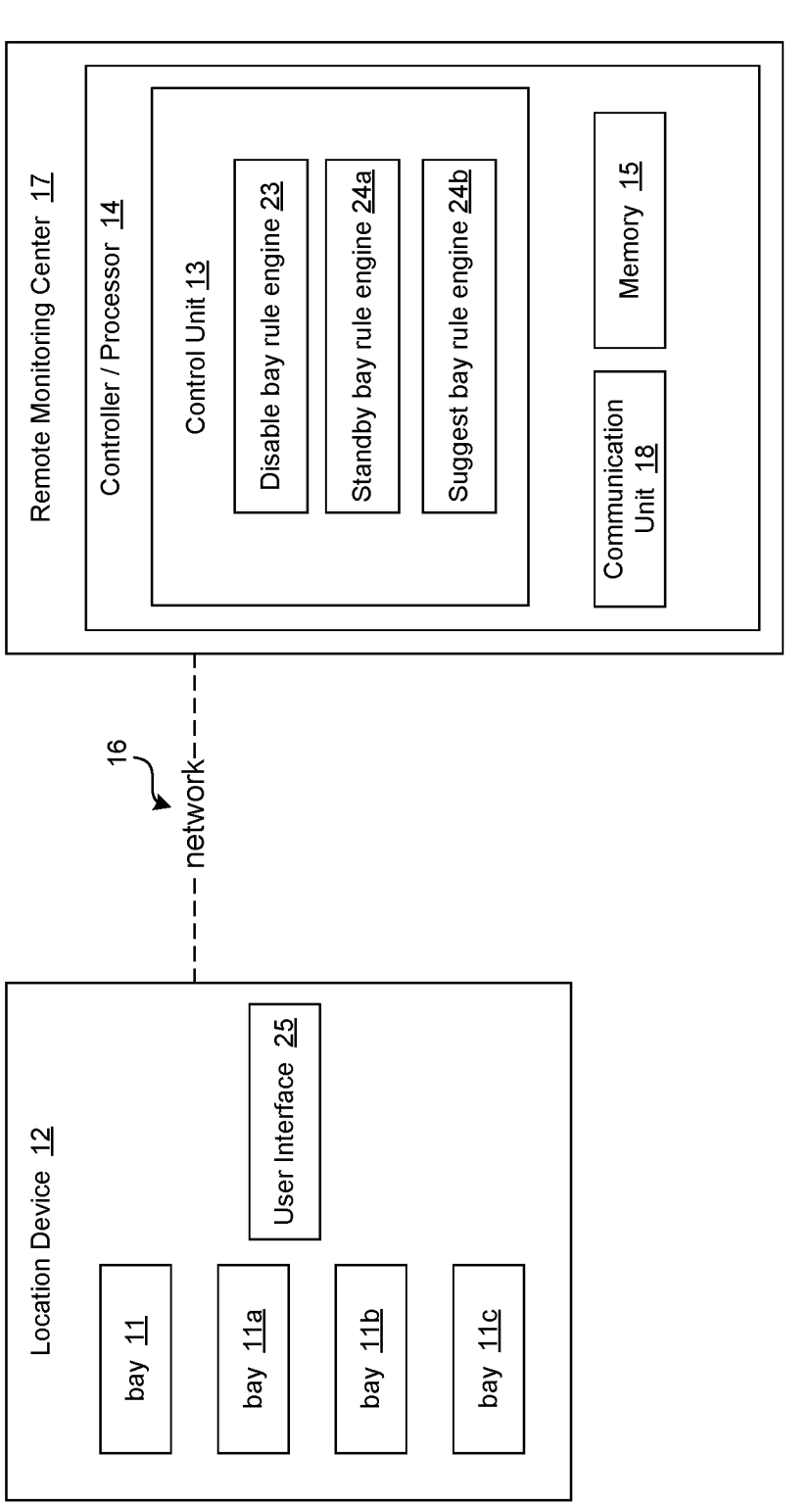
FIG. 2 is a block diagram of a remote monitoring system for a diagnostic instrument in accordance with the principles of the present technology.

FIG. 2 shows an example embodiment of the remote monitoring system 17 in communication with an example embodiment of the location device 12, e.g., via the network 16. The location device 12 includes multiple bays (e.g., bay 11, bay 11*a*, bay 11*b*, bay 11*c*) and the user interface 25; and the remote monitoring center 17 includes the controller/ processor 14, comprising the communication unit 18, the memory 15, and an example embodiment of the control unit 13.

Control Unit

Figure 4:
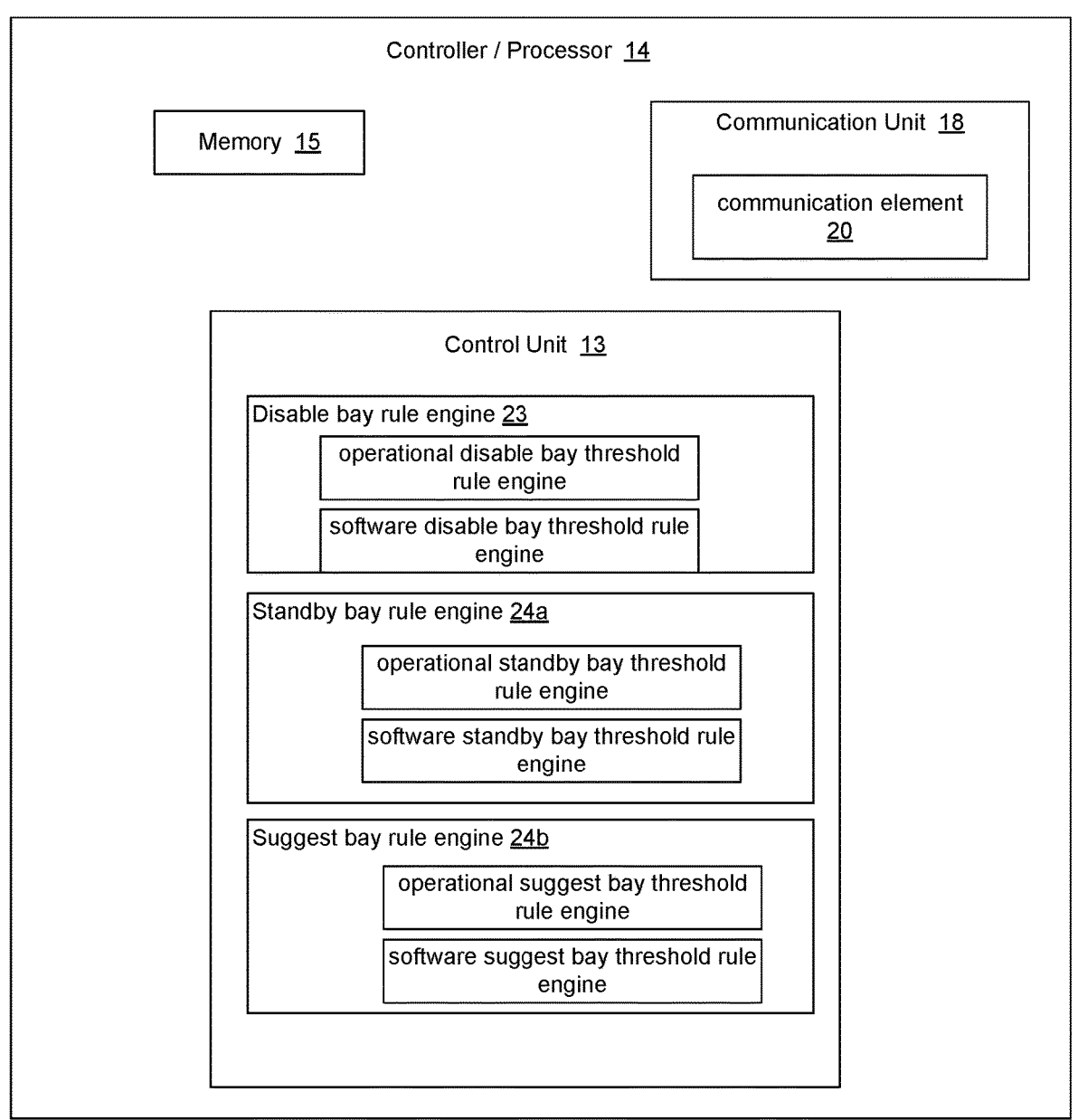
FIG. 4 is a block diagram of a controller/processor in accordance with the principles of the present technology.

FIG. 4 shows an example control unit 13 for analyzing a location-based instrument's run data. Control unit 13 may include analysis rule engines such as a disable bay rule engine, standby bay rule engine, suggest bay rule engine, assess bay rule engine or combinations thereof. Each of these rule engines may have its own operational threshold rule engine and/or software threshold rule engine. In some embodiments, the control unit generates the run data, the evaluate data, the disable bay data, the standby bay data, the suggest bay data and combinations thereof.

Processor

The processor 14 (FIG. 1, FIG. 2, and FIG. 4) communicates with and/or controls the bays 11 and/or user interface 25 (e.g., GUI). In some embodiments, the processor 14 communicates with the network 16.

Processor 14 may communicate with network 16 via communication unit 18. Communication system 18 may comprise one or more communication links such as wired or wireless communication links, e.g., Wi-Fi and/or other technologies. For example, the communication links may be broadband communication links such as a wired cable modem or Ethernet communication link, and a digital cellular communication link, e.g., long term evolution (LTE) based link, among other broadband communication links known in the art. Broadband as used herein may refer to a communication link other than a plain old telephone service (POTS) line. An Ethernet communication link may be an IEEE 802.3 based communication link. The network 16 may be a wide area network, local area network, wireless local network or metropolitan area network, among other networks known in the art. Network 16 provides communications between processor 14 and remote monitoring center 17, e.g., as illustrated in FIG. 1.

In some implementations, the processor 14 performs the disable bay monitoring procedure and analysis. In some implementations, the processor 14 collects disable bay monitoring data. Processor 14 determines whether a disable bay issue exists, e.g., is the disable bay data below a predefined limit. If the processor determines an issue exists, processor 14 may disable the bay.

In some implementations, the processor 14 performs the standby monitoring procedure and analysis. Processor 14 collects standby monitoring data. Processor 14 determines whether a standby issue exists, e.g., is the standby bay data below a predefined limit. If the processor determines an issue exists, processor 14 may put the bay on standby.

In some implementations, the processor 14 performs the suggest monitoring procedure and analysis. Processor 14 collects suggest monitoring data. Processor 14 determines whether a suggest issue exists, e.g., is the suggest bay data below a predefined limit. If the processor determines an issue exists, processor 14 may suggest the bay.

In some implementations, the processor 14 performs the assess monitoring procedure and analysis. Processor 14 collects assess monitoring data. Processor 14 determines whether an assess issue exists, e.g., is the bay run data below a predefined limit. If the processor determines an issue exists, processor 14 may put the bay on standby, suggest the bay or disable the bay.

In some implementations, the processor 14 performs the evaluate monitoring procedure and analysis. Processor 14 collects evaluate monitoring data. Processor 14 determines whether an evaluate issue exists, e.g., is the evaluate data below a predefined limit. If the processor determines an issue exists, processor 14 may put the bay on standby, suggest the bay or disable the bay.

Communication System

Communication system 18 may include a communication element (shown in FIG. 4, and not shown in FIG. 1, FIG. 2), which can be a wired or wireless communication device. The communication element provides communication with the bays 11 and user interface 25. In some implementations, the communication element may support one or more wireless communication protocols such as Zigbee, Z-Wave and Wi-Fi, e.g., IEEE 802.11, among other wireless communication protocols that support wireless or wired data transfer.

In some implementations, the communication element enables location device 12 and/or processor 14 to be used with a variety of interfaced devices and integrated with various equipment vendors.

Remote Monitoring Center

As shown in FIG. 1, in some embodiments, the remote monitoring center 17 performs monitoring, configuration and/or control functions associated with processor 14 and/or control unit 13. For example, the remote monitoring center 17 may include a remote assess bay monitoring system and/or remote disable bay monitoring system and/or a standby monitoring system and/or a suggest monitoring system that monitors bays 11 on the location device 12 and controls the user interface 25. In some embodiments, the remote monitoring center receives run data, evaluation data, disable bay data, suggest bay data and/or standby bay data from the location device's communication network 18.

In some implementations, the remote monitoring center 17 includes a remote communication element 21, e.g., an Ethernet based hardware component that provides communication with network 16. Alternatively, or in addition to the Ethernet based hardware component, remote communication element 21 may include a Wi-Fi (IEEE 802.11) hardware component that provides communication with the location device or other networked devices.

In some implementations, the remote monitoring center 17 includes disable control element 22, which can be used by a user to disable a bay remotely and manually, suggest a bay or put a bay on standby on a location device. Disable control element 22 allows for an alternative or back-up way of disabling a bay, suggesting a bay or putting a bay on standby on a location device that does not require self-monitoring by the device or monitoring by a remote monitoring system.

In some embodiments, the run data, the evaluate data, the disable bay data, the standby bay data, the suggest bay data and combinations thereof is shared with the remote monitoring system. The remote monitoring system compiles the run data, the evaluate data, the disable bay data, the standby bay data, the suggest bay data and combinations thereof from multiple diagnostic instruments. The combined run data is used to form the historical run data, the historical evaluate data, the historical disable bay data, the historical standby bay data, the historical suggest bay data and combinations thereof. Then the historical run data, the historical evaluate data, the historical disable bay data, the historical standby bay data, the historical suggest bay data and combinations thereof is used by the rule engines on the particular instrument of interest.

GUI

Figure 3:
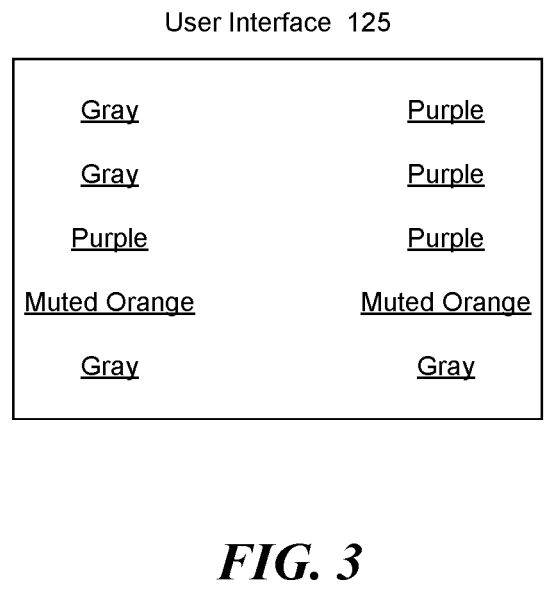

FIG. 3 shows an example embodiment of the user interface 25, shown as user interface 125 in FIG. 3. In some embodiments, the user interface 25 (and user interface 125) is a GUI. A GUI may include one or more indicators such as colors that may indicate the status of the bay. For example, a first color is used when the bay is disabled, a second color is used when the bay is suggested, a third color is used when the bay is on standby wherein the first color, second color and third color are different. In some embodiments, the bay has different colors for when the bay is available, in operation or a run is complete.

In some embodiments, the processor 14 communicates with the GUI. In some embodiments, the GUI is controlled by the processor 14. In some embodiments, the GUI communicates with the remote monitoring center 17. In some embodiments, the GUI is controlled by the remote monitoring center 17.

Bay Door Lights

As shown in FIG. 1, in some embodiments, each bay has a light. The bay light includes one or more indicators such as colors that may indicate the status of the bay. For example, a first color is used when the bay is disabled, a second color is used when the bay is suggested, a third color is used when the bay is on standby wherein the first color, second color and third color are different. In some embodiments, the bay has different colors for when the bay is available, in operation or a run is complete.

In some embodiments, the processor 14 communicates with the bay light. In some embodiments, the bay light is controlled by the processor 14. In some embodiments, the bay light communicates with the remote monitoring center 17. In some embodiments, the bay light is controlled by the remote monitoring center 17.

Bay Door Lock

In some embodiments, each bay has a door lock (not shown). In some embodiments, the processor 14 communicates with the bay door lock and locks it or unlocks it based on the status of the bay. In some embodiments, the bay door lock communicates with the remote monitoring center 17 and the remote monitoring center 17 locks the bay door or unlocks it based on the status of the bay. In some embodiments, the bay door is locked when the run data (such as disable bay data) is at or below a threshold. In some embodiments, the bay door is locked when the run data (such as standby bay data) is within a standby threshold range. In some embodiments, the bay door is unlocked when the run data (such as standby bay data) is within a standby threshold range. In some embodiments, the bay door is unlocked when the run data (such as suggest bay data) is above a threshold. In some embodiments, the bay door is locked when the evaluation data is above a threshold, below a threshold or within a range. In some embodiments, the bay door is unlocked when the evaluation data is above a threshold, below a threshold or within a range.

Memory

In some embodiments, the memory 15 on the location device may include nonvolatile and volatile memory. For example, nonvolatile memory may include a hard drive, memory stick, flash memory and the like. Also, volatile memory may include random access memory and others known in the art. Memory 15 may store disable bay data and standby bay data or suggest bay data among other data and/or rule engines. In FIG. 1, the memory 15 is shown as part of the processor 14. In FIG. 4, the memory 15 is shown outside of the control unit. Alternatively, the memory 15 can be outside and/or inside the control unit.

Memory 15 may include historical threshold disable bay data, historical threshold standby bay data, historical threshold suggest bay data among other data.

Any bay data (e.g., disable bay data, suggest bay data, standby bay data, run data and/or evaluation data) can be stored in the processor's memory or in the remote monitoring center 17.

Disable Bay Self-Monitoring Rule Engine

The disable bay rule engine 23 (also referred to as the disable bay monitoring system or disable rule engine) includes instructions which, when executed by processor 14, cause processor 14 to perform the disable bay monitoring process.

In some embodiments, the disable bay rule engine 23 evaluates the disable bay data (or another type of data such as evaluate bay data) by comparing it to disable bay threshold data. In some embodiments, if the disable bay data passes the disable bay rule engine 23, the analysis of the disable bay data ends.

In some embodiments, if the disable bay data passes the disable bay rule engine 23, the disable bay data is then considered by another rule engine such as the standby rule engine (also referred to as standby bay rule engine). The standby rule engine evaluates the disable bay data by comparing it to standby bay threshold data. If the disable bay data passes the standby rule engine, the disable bay data is then considered by another rule engine such as the suggest rule engine. The suggest rule engine evaluates the disable bay data by comparing it to suggest bay threshold data.

In some embodiments, the disable bay rule engine 23 first evaluates the disable bay data (or another type of data such as evaluate bay data) by comparing it to disable bay threshold data. If the disable bay data does not pass the disable bay rule engine 23, the disable bay data is not then considered by another rule engine. If the disable bay data passes the disable bay rule engine 23, the disable bay data is then considered by another rule engine.

In some embodiments, the disable bay data is only evaluated by the disable bay rule engine 23.

Standby Self-Monitoring Rule Engine

In some embodiments, the standby monitoring rule engine 24a (also referred to as the standby monitoring system or standby bay rule engine) includes instructions which, when executed by processor 14, cause processor 14 to perform the standby monitoring process.

In some embodiments, the disable bay rule engine 23 evaluates the standby bay data (or another type of data such as evaluate bay data) by comparing it to disable bay threshold data. If the standby bay data passes the disable bay rule engine 23, the standby bay data is then considered by the standby bay rule engine 24a. The standby bay rule engine 24a evaluates the standby bay data by comparing it to standby bay threshold data. If the standby bay data passes the standby bay rule engine 24a, the standby bay data is then considered by the suggest bay rule engine 24b. The suggest bay rule engine 24b evaluates the standby bay data by comparing it to suggest bay threshold data.

In some embodiments, the standby bay rule engine 24a first evaluates the standby bay data (or another type of data such as evaluate bay data) by comparing it to standby bay threshold data. If the standby bay data fails the standby bay rule engine 24a, the standby bay data is not then considered by another rule engine. If the standby bay data passes the standby bay rule engine 24a, the standby bay data is then considered by another rule engine.

In some embodiments, the standby bay data is only evaluated by the standby bay rule engine 24a.

Suggest Self-Monitoring Rule Engine

In some embodiments, the suggest monitoring rule engine 24b (also referred to as the suggest monitoring system, suggest bay rule engine, or suggest rule engine) includes instructions which, when executed by processor 14, cause processor 14 to perform the suggest monitoring process.

In some embodiments, the disable bay rule engine evaluates the suggest bay data (or another type of data such as evaluate bay data) by comparing it to disable bay threshold data. If the suggest bay data passes the disable bay rule engine, the suggest bay data is then considered by the standby rule engine 24*a*. The standby rule engine 24*a* evaluates the suggest bay data by comparing it to standby bay threshold data. If the suggest bay data passes the standby rule engine 24*a*, the suggest bay data is then considered by the suggest rule engine 24*b*. The suggest bay rule engine 24*b* evaluates the suggest bay data by comparing it to suggest bay threshold data.

In some embodiments, the suggest bay rule engine 24*b* first evaluates the suggest bay data (or another type of data such as evaluate bay data) by comparing it to suggest bay threshold data. If the suggest bay data passes the suggest bay rule engine 24*b*, the suggest bay data is not then considered by another rule engine. If the suggest bay data does not pass the suggest bay rule engine 24*b*, the suggest bay data is then considered by another rule engine.

In some embodiments, the suggest bay data is only evaluated by the suggest bay rule engine 24*b*.

In some embodiments, a single data set (evaluation data) is evaluated by each of the disable bay rule engine 23, standby bay rule engine 24*a*, suggest bay rule engine 24*b* and combinations thereof Assess Self-Monitoring Rule Engine In some embodiments, the assess monitoring rule engine 24*c* (not shown) (also referred to as the assess monitoring system, assess bay rule engine, or assess rule engine) includes instructions which, when executed by processor 14, cause processor 14 to perform the assess monitoring process. (See FIG. 11.)

In some embodiments, the assess bay rule engine evaluates the bay run data (or another type of data such as evaluate bay data) by comparing it to assess threshold data in the assess rule engine. If the bay run data passes the assess bay threshold data, the bay is suggested. If the bay run data falls within the standby bay threshold data range, then the bay is placed on standby. If the bay run data is at or above the disable bay threshold data, then the bay is disabled.

In some embodiments, the assess bay rule engine first evaluates the bay run data (or another type of data such as evaluate bay data) by comparing it to assess bay threshold data with the assess rule engine. If the bay run data passes the assess rule engine, the bay run data is not then considered by another rule engine. If the assess bay run data does not pass the assess rule engine, the bay run data is then considered by another rule engine.

In some embodiments, the bay run data is only evaluated by the assess bay rule engine.

Software Architecture

Figure 5:
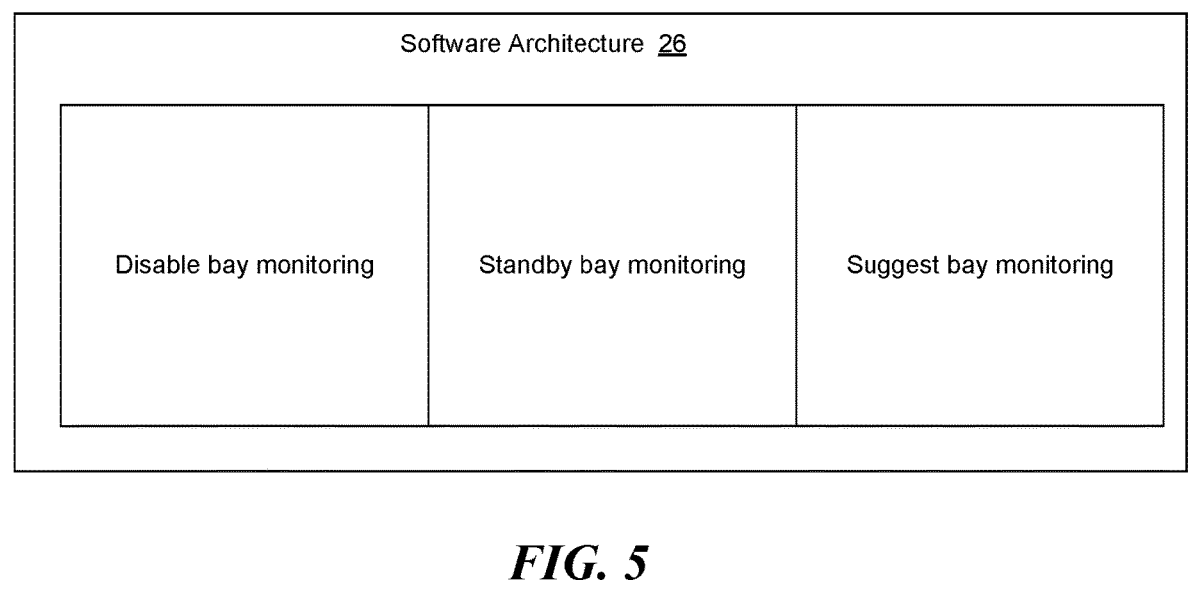

FIG. 5 shows an exemplary software architecture 26 of processor 14. In some embodiments, the software architecture 26 may include disable bay monitoring, standby bay monitoring, suggest bay monitoring, assess bay monitoring among other software components relating to location-based instrument monitoring, operation and control. Disable bay monitoring, standby bay monitoring, suggest bay monitoring, assess bay monitoring and combinations thereof are configured to run in processor 14 or control unit 13 or both.

In some embodiments, disable bay monitoring and/or standby bay monitoring and/or suggest bay monitoring and/or assess bay monitoring can be run at predetermined intervals and/or may initiate monitoring upon receipt of a command to run monitoring. In another example, processor 14 may determine to initiate monitoring upon request by an on-site technician, by a remote user, upon power up of the instrument and/or may periodically initiate monitoring. In another example, processor 14 may initiate monitoring after each sample is processed. In another example, processor 14 may initiate monitoring after a predetermined number of samples are processed, i.e., after 2 samples are processed or after 10 samples are processed or after 50 samples are processed. As used herein, monitoring means data analysis, i.e., run data analysis, evaluation data analysis, disable bay run data analysis, standby bay run data analysis, suggest bay run data analysis or combinations thereof. As used herein, data analysis means comparing the run data to threshold data. As used herein, threshold data (e.g., historical threshold data) is based on data collected over time. For example, a threshold may be placed at four invalids out of the last four runs based on historical data showing that once invalid runs exceed that frequency, more failures may occur. Or, a threshold may be placed at 500 nanoamps (nA) because below that threshold the system cannot accurately detect signal. The threshold may be based on samples run on or off the current bay being analyzed.

The command to monitor (perform the disable bay analysis, standby bay analysis, suggest bay analysis, assess bay analysis or combinations thereof) the bays may be transmitted from the user interface 25 on the location device 12 and/or remote monitoring center 17. The command may indicate whether to initiate or skip disable bay monitoring, standby bay monitoring, suggest bay monitoring, assess bay monitoring or combinations thereof.

Reports

In some embodiments, the processor 14 may generate a report with the results of the disable bay monitoring procedure, standby bay monitoring procedure, suggest bay monitoring procedure, assess bay monitoring procedure, evaluate bay monitoring procedure and combinations thereof (See FIGS. 6, 7, 8 and 11.) The report may contain details on one or more actions that were taken (disable bay, suggest a bay or put a bay on standby). The report may be printed by the diagnostic instrument or it may be sent to the network 16.

The data generated by the diagnostic instrument indicates whether one or more devices and/or functions of a location-based system are operating and/or will continue to operate as designed. The report and metrics included in the report may be stored in memory 15 for future comparison with an updated report generated by the processor 14, i.e., in some embodiments the processor 14 tracks a health history of the location-based system to identify persistent problems and problems that have been fixed.

In some embodiments, the report is transmitted to a user interface device (not shown) or the network 16 and/or remote monitoring center 17, or to other devices, servers and/or users. For example, an on-site technician may review the report in order to troubleshoot system issues. In another example, a remote monitoring center may dispatch an on-site technician based on the report received from the location device 12.

Disable Bay Monitoring Procedure

Figure 6:
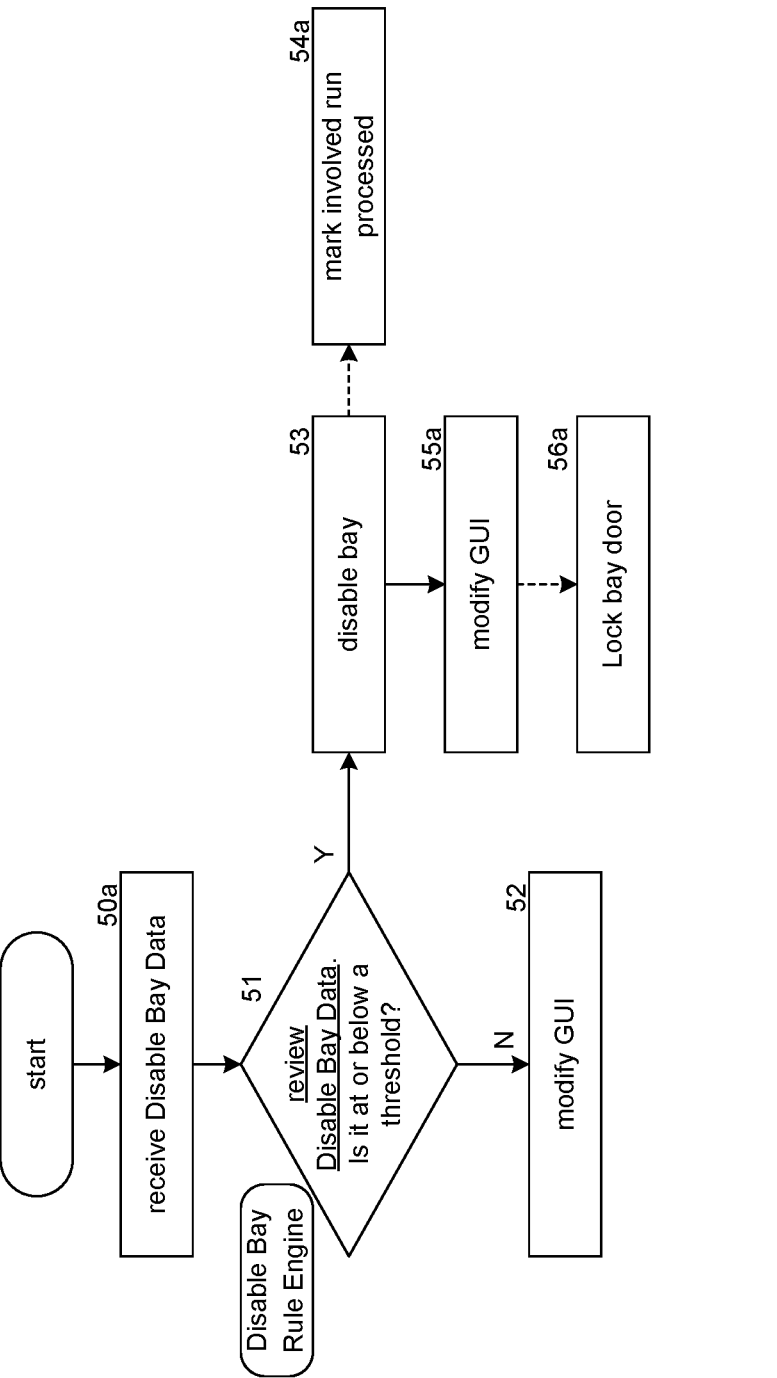
FIG. 6 is a flow chart of a disable bay monitoring procedure in accordance with the principles of the present technology.

FIG. 6 shows an example disable bay monitoring procedure of disable bay rule engine 23. In some embodiments, the outcome of a disable bay rule analysis is to either disable a bay, put a bay on standby, allow the bay to be used or suggest a bay to be used. In some embodiments, the outcome of a disable bay rule analysis is to either disable a bay or perform a standby bay monitoring procedure and/or a suggest bay monitoring procedure.

As shown in the example of FIG. 6, the processor 14 receives data from the control unit 13 (at process 50a). The processor 14 reviews the disable bay data (at process 51) with the disable bay rule engine. In some embodiments of the process 51, the review means the processor 14 compares the disable bay data to historical disable bay data run on that processor, historical disable bay data received from other bays on that instrument, historical disable bay data received from other bays from other instruments and combinations thereof.

In some embodiments, if the disable bay data is above a predetermined limit (e.g., disable bay threshold), the user interface 25 (e.g., GUI) is modified to show that the bay is ready to process another sample (at process 52). In some embodiments, when the disable bay data is at or below a predetermined limit, the bay is disabled to prevent it from processing another sample (at process 53). In this example, the bay is disabled at process 53 when the disable bay data is determined at or below the threshold; yet it is understood that the threshold can be set to indicate the bay needs to be disabled when the disable bay data is just above the threshold value; and vice versa.

In some embodiments, for example, when the disable bay data is below a predetermined limit and the bay has been disabled (at process 53), the user interface 25 (e.g., GUI) is modified to indicate that the bay has been disabled (at process 55a). In some embodiments, when the disable bay data is below a predetermined limit, the bay icon corresponding to the bay at issue on the GUI is modified to indicate that the bay has been disabled. In some embodiments, when the disable bay data is below a predetermined limit, the bay icon is gray on the GUI to indicate that the bay has been disabled.

In some embodiments, when the disable bay data is below a predetermined limit, the sample is marked "processed," for example, at process 54a. In some embodiments, when the bay is disabled in response to disable bay data, the results from the sample analyzed are still reported. In some embodiments, when the bay is disabled in response to disable bay data, the results from the sample analyzed are not reported.

In some optional embodiments, when the disable bay data is below a predetermined limit (e.g., disable bay threshold), the bay door is locked (at process 56a) to prevent insertion of another cartridge. In some embodiments, when the disable bay data is below a predetermined limit, the bay door is not locked and if a sample is inserted into the bay, the processor ejects the cartridge without processing it.

In some embodiments, when the disable bay data is below a predetermined limit, the bay door is disabled to prevent processing of another sample. Disabling the bay (e.g., such as disabling the bay door) may include failure to supply power to the bay, deletion or disablement of software protocols controlling the bay, disabling pumps, locking the bay door, ejecting a cartridge, displaying an error message when the bay icon is selected, and combinations thereof.

In some instances, the disable bay outcome and the standby bay outcome are in a toggle relationship: if not disabled, then put the bay on standby. In some instances, the disable bay outcome and the suggest bay outcome are in a toggle relationship: if not disabled, then suggest the bay, or, if not suggested, then disable the bay. In some instances, the suggest bay outcome and the standby bay outcome are in a toggle relationship: if not on standby, then suggest the bay, or, if not suggested, then put the bay on standby. In some instances, the disable bay outcome and the suggest bay outcome are in a toggle relationship: if not disabled, then suggest the bay, or, if not suggested, then disable the bay.

In some embodiments, if the disable bay data is above a predetermined limit (e.g., disable bay threshold), the bay is not disabled, and the user interface 25 (e.g., GUI) is modified to indicate that the bay is ready to process another sample (at process 52).

In some embodiments, the disable bay data is compared to at least one disable bay threshold, and if it is at or above the threshold, the sample is processed.

In one embodiment, when the user taps on a bay icon that has been modified because the bay data does not meet a minimum threshold disable bay rule, the following message appears: Bay AI has been automatically disabled (WR1). Please contact Technical Support.

In some embodiments, the disable bay threshold is a range, is a magnitude or intensity that must be exceeded for a certain condition to be met or is a combination thereof. Operational Disable Bay Monitoring Rule Engine and Software Disable Bay Monitoring Rule Engine.

In some embodiments, the processor 14 receives data from the control unit 13 (at process 50a). In some embodiments, the processor 14 reviews the disable bay data (at process 51) for operational issues in the operational disable bay rule engine. In some embodiments, the processor 14 reviews the disable bay data (at process 51) for software issues in the software disable bay rule engine. In some embodiments, the processor 14 reviews the disable bay data (at process 51) for operational issues in the operational disable bay rule engine and software issues in the software disable bay rule engine.

In some embodiments, the processor 14 reviews the disable bay data (at process 51) for operational issues by evaluating if operating conditions meet operational disable bay baseline(s). Operational disable bay baselines include one or more predefined thresholds that indicate, when met, the location device 12 or the bay (e.g., bay 11a, 11b or 11n) currently has at least one hardware or firmware issue/problem.

In some embodiments, the processor 14 reviews the disable bay data (at process 51) for software issues by evaluating if software disable bay baseline(s) are met. Software disable bay baselines include one or more predefined thresholds that indicate, when met, the location device 12 or the bay (e.g., bay 11a, 11b or 11n) currently has at least one software issue/problem.

In some embodiments, the disable bay threshold data will reveal that a bay in a particular location always performs poorly even when the bay is replaced. In such situations, the disable bay threshold data will always keep that bay disabled even if it passes all the rule engines.
Disable Bay Monitoring Rules/Threshold Data Analysis.

Disable bay monitoring rules are the rules which define the disable bay monitoring procedure of disable bay rule engine 23. In some embodiments, disable bay monitoring rules are predefined for the instrument by a user. In some embodiments, disable bay monitoring rules are created by artificial intelligence that evaluates run data and establishes a new disable bay monitoring rule to be applied on the instrument. The disable bay monitoring rules form the disable bay threshold data.

In one embodiment, memory 15 may store the disable bay monitoring rules. The disable bay monitoring rules may relate to the control unit 13, the bays (e.g., bay 11), other components of the location device, other components of the system or combinations thereof.

As one example, a disable bay monitoring rule may include: When the location device experiences four consecutive errors, disable the bay. In some embodiments, four consecutive errors occur when there are four consecutive invalid runs (that have not been processed by a previous auto-disabled event) in a row on a bay. In some embodiments, four consecutive errors occur when there are four consecutive invalid runs (that have not been processed by a previous auto-disabled event) in a row on a bay with certain validity codes. In some embodiments, four consecutive errors occur when there are four consecutive invalid runs (that have not been processed by a previous auto-disabled event) in a row on a bay with certain validity codes wherein the validity codes come from any combination of assay types. For example, all four validity codes may come from a first assay type. For example, all four validity codes may come from four different assay types. For example, a first validity code may come from a first assay type and three validity codes may come from a second assay type. For example, a first and second validity code may come from a first assay type and the third and fourth validity codes may come from a second assay type. The assay types may be, for example, blood culture identification panels, respiratory panels, gastrointestinal panels, HCVg Test, Cystic Fibrosis Genotyping Test, Thrombophilia Risk Test, Warfarin Sensitivity Test, 2C19 Genotyping Test.

In some embodiments, once a bay is auto disabled, the runs involved will be marked "processed" and excluded from the disable bay monitoring rule consideration in the future.

In some embodiments, the disable bay monitoring rule is checked after each run, i.e., after each sample is processed by the instrument.

In some instances, the disable bay data is collected after a sample is processed. In some instances, the disable bay data is collected before a sample is processed. For example, if a bay fails to connect to four or more cartridges in a row, the disable bay monitoring rule is met, and the bay is disabled. In some instances, failure to connect is determined by impedance data.

It is noted in FIG. 6 (and other example block diagram flow charts), the order of Blocks (processes) 50-56 is not limited to the order shown in the diagram, and the blocks (processes) may be performed in a different order based on design need. Further, one or more blocks may be skipped or omitted from FIG. 6 based on design need, e.g., Blocks (process) 54 and/or 56 may be skipped or omitted.

Processor 14 determines whether an issue exists, e.g., is the disable bay data below a predefined limit. If the processor determines an issue exists, processor 14 may disable the instrument or disable the bay or combinations thereof.

The disable bay monitoring rule (e.g., threshold data) for a first location device may be the same as, more than and/or less than a disable bay monitoring rule (threshold data) for a second location device.

The disable bay threshold (e.g., monitoring rule) for a first bay may be the same as, more than and/or less than a disable bay threshold (e.g., monitoring rule) for a second bay on that same device. The disable bay threshold for a first bay may be the same as, more than and/or less than a disable bay threshold for a first bay on a different device.

The disable bay monitoring rule (e.g., threshold data) for a bay may change over time.

Modification.

In some embodiments, if a disable bay monitoring rule (e.g., threshold data) is violated, the processor 14 may optionally modify at least one setting of location device 12.

The light on the bay door may be changed to indicate its disabled status. For example, the light on the bay door may be changed to gray to indicate its disabled status. For example, the icon color on the user interface corresponding to the bay may be changed to indicate its disabled status. For example, the icon color on the user interface corresponding to the bay may be changed to gray to indicate its disabled status. For example, the bay door may be locked. For example, the power to the bay may be discontinued. In addition to modifying the bay icon or bay door light color, in some embodiments, the processor may modify one or more bay 11 settings and/or user interface 25 settings when a disable bay rule is violated. For example, if a heater cannot reach the desired temperature, a bay fan may be turned on to improve temperature control.

In some embodiments, if a disable bay monitoring rule is not violated, the processor 14 may optionally modify at least one setting of location device 12. In some embodiments, the processor may modify one or more bay 11 settings and/or user interface 25 settings when a disable bay rule is not violated. For example, the light on the bay door may be changed to indicate its status. For example, the light on the bay door may be changed to white to indicate its status is ready to process another sample. For example, the icon color on the user interface corresponding to the bay may be changed to indicate its status. For example, the icon color on the user interface corresponding to the bay may be changed to white to indicate its ready to run status.

In some embodiments, when no disable bay monitoring rules are violated, the bay is suggested. In some embodiments, when no disable bay monitoring rules are violated, the bay is put on standby. In some embodiments, when no disable bay monitoring rules are violated, the bay status remains neutral, e.g., is not disabled, suggested or put on standby.

Alerts.

Referring back to FIG. 6, Block 51, if processor 14 determines an issue does not exist (i.e., a disable bay rule is not violated), processor 14 may end the disable bay monitoring procedure. In some instances, when a disable bay threshold rule is satisfied, a disable bay pass alert may be transmitted to user interface 25, the network 16, the remote monitoring center 17 and combinations thereof. The disable bay pass alert may indicate the one or more issues that were assessed have passed inspection or it may simply indicate that the system/bay is ready.

In some instances, when a disable bay rule is not satisfied, a disable bay fail alert may be transmitted to user interface 25, the network 16, the remote monitoring center 17 and combinations thereof. The disable bay fail alert may indicate the one or more issues that were assessed have failed inspection or it may simply indicate that the system/bay has been disabled.

Standby Monitoring Procedure

Diagnostic instruments commonly require some preventive and/or corrective maintenance on an ongoing basis. In practice, such preventive and/or corrective maintenance is often neglected, leading to less efficient detection of pathogens. In many cases, the diagnostic instruments are operated until failure, and then a technician is called to make repairs. Such a reactive approach to maintenance increases the costs associated with operating the diagnostic instrument, leads to delay in reporting results, and leads in some cases to death of a patient, such as in the case of a sepsis diagnosis when every hour of delay results in an increased mortality of 7.4%.

Currently, customers and instrument providers have no way of knowing when the health levels of diagnostic instruments are going to degrade to the point that functionality, i.e., ability to detect an analyte, is diminished or eliminated. Such a failure may come at an inopportune time, such as when the customer is experiencing a rush in demand or over a weekend when service is harder to obtain, etc. Thus, it would be helpful to predict when a bay will cease functioning and turn it off before it reaches that point.

Figure 7:
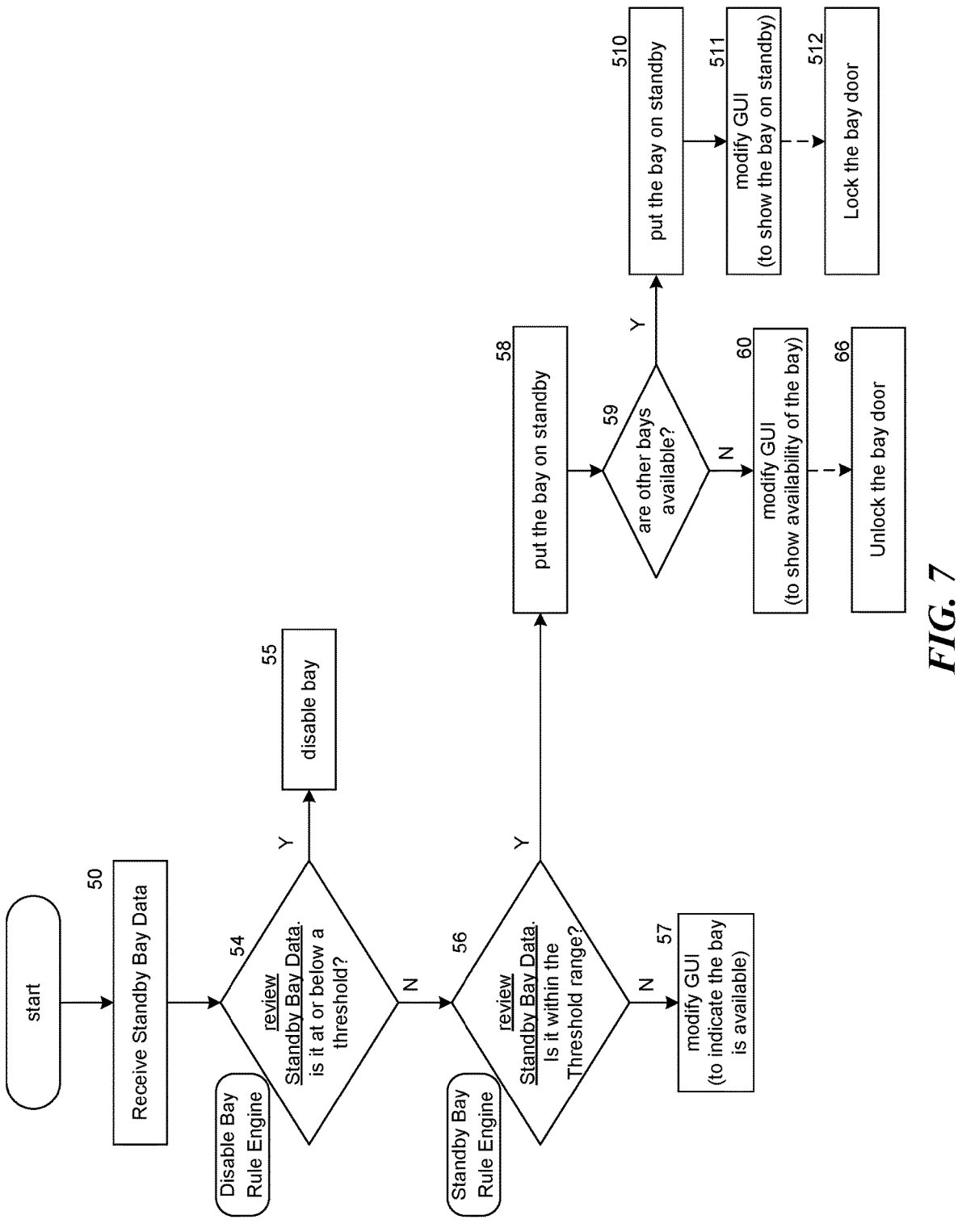
FIG. 7 is a flow chart of a standby bay monitoring procedure in accordance with the principles of the present technology.

FIG. 7 shows an example standby monitoring procedure of standby rule engine 24*a*. In some embodiments, the outcome of a standby rule analysis is to either put a bay on standby or suggest a bay. In some embodiments, the outcome of a standby rule analysis is to disable a bay.

As shown in FIG. 7, the processor 14 receives standby bay data from the control unit 13 (at process 50). In some embodiments, the processor 14 first reviews the standby bay data (at process 54) with the disable bay rule engine. If the standby bay data is within a threshold range (e.g., at or below a predetermined threshold), the bay is disabled (at process 55). The process 55 may be implemented in accordance with embodiments previously discussed in connection with the process 53 (in FIG. 6).

In implementations of the process 54, when the disable bay data is not within the threshold range (e.g., above the predetermined threshold), then the processor 14 reviews the standby bay data (at process 56) with the standby bay rule engine. If, at process 56, the standby bay data is not within a threshold range (e.g., above a predetermined baseline), the user interface 25 (e.g., GUI) is modified (at process 57) to show that the bay is available to process another sample. In implementations of the process 56, when the standby bay data is within the threshold range (e.g., below a predetermined limit), the bay is put on standby (at process 58). In some embodiments, when the bay is determined to be put on standby at the process 56, the user interface 25 (e.g., GUI) is modified to indicate that the bay has been placed on standby. For example, the sample is marked "processed." Also, for example, in some implementations, when the standby bay data is above the predetermined baseline, the sample is marked "processed."

In some embodiments, when the bay is to be put on standby (at the process 58), the processor 14 evaluates whether there are other available bays (at process 59). At process 59, if the standby bay data is determined to be within a range of threshold data (e.g., below a predetermined baseline) that indicates there are no other available bays, the user interface 25 (e.g., GUI) is modified (at process 60) to show that the bay is being made available (or suggested) to process the sample. Whereas, in some embodiments at process 59, it is determined that a bay is available by default, or when a bay comes out of a condition (e.g., such as disabled, standby, or suggested) it becomes available. For example, when it is determined that there are no other bays available (at process 59), the system is configured to allow the user to run the sample in the bay. When no other bays are available, the system can modify the GUI to show the bay is available (at process 60) to allow the sample to be run. When other bays are available, the system (at process 510) will put the bay on standby (e.g., maintain from process 58), and may perform other functions at processes 511 and/or 512, discussed below. In some optional embodiments, for example, when it is determined (at process 59) there are not other available bays, the bay door can be unlocked (at process 66) if the bay had previously been put on standby and the bay door locked.

In some embodiments, when it is determined (at process 59) there are other available bays, the bay is put (e.g., maintained) on standby (at process 510). In some embodiments, when there are other available bays and the bay is put on standby at process 510, the user interface 25 (e.g., GUI) is modified to indicate that the bay has been placed on standby (at process 511). In some optional embodiments, for example, when it is determined (at process 59) there are other available bays and the bay is put on standby (process 510), the bay door is locked (at process 512).

In some embodiments, the standby bay data is evaluated by the disable bay rule engine before the standby rule engine. In some embodiments, the standby bay data is evaluated by the standby rule engine before the disable bay rule engine. In some embodiments, the standby bay data is evaluated by the standby rule engine without performing the disable bay rule engine. In some embodiments, the standby bay data is evaluated by the disable bay rule engine without performing the standby analysis by the standby rule engine.

In some embodiments, the standby bay data is compared to at least one standby baseline, and if it is below the baseline (e.g., standby bay threshold data), the bay is put on standby. In some embodiments, the standby bay data is compared to at least one standby baseline, and if it is above the baseline, the bay is suggested. In some embodiments, the standby bay data is compared to at least one predetermined or predefined baseline, and if it is at or above the baseline, the bay is ready for another sample.

In some embodiments, the standby bay threshold data is based on the past performance of the bay being analyzed, based on the past performance of other bays on the same instrument being analyzed, based on the past performance of other bays on other instruments than the one being analyzed and combinations thereof.

The standby bay threshold data indicates whether at least one of the bays is likely to operate within a failure range within a predefined window. The window can be a time frame or number of samples processed. For example, the bay is predicted to fail within the next three runs.

Operational Standby Monitoring Rule Engine and Software Standby Monitoring Rule Engine.

In some embodiments, the processor 14 receives data from the control unit 13 (at process 50). In some embodiments, the processor 14 reviews the standby bay data (at process 56) for operational issues in the operational standby rule engine. In some embodiments, the processor 14 reviews the standby bay data (at process 56) for software issues in the software standby rule engine. In some embodiments, the processor 14 reviews the standby bay data (at process 56) for operational issues in the operational standby rule engine and software issues in the software standby rule engine.

In some embodiments, the processor 14 reviews the standby bay data (at process 56) for operational issues by evaluating if operating conditions meet operational standby baseline(s). Operational standby baselines include one or more predefined thresholds that indicate, when met, the location device 12 or the bay (e.g., bays 11*a*, 11*b* or 11*n*) is currently likely to develop at least one hardware or firmware issue/problem.

In some embodiments, the processor 14 reviews the standby bay data (at process 56) for software issues by evaluating if software standby baseline(s) are met. Software standby baselines include one or more predefined thresholds that indicate, when met, the location device 12 or the bay (e.g., bays 11*a*, 11*b* or 11*n*) is likely to develop at least one software issue/problem.

Standby Monitoring Rules/Threshold Data Analysis.

Standby monitoring rules (also referred to as threshold data) are the rules which define the standby monitoring, procedure of standby rule engine 24a. The outcome of a standby rule may either suggest a bay, disable a bay or put a bay on standby.

In some embodiments, standby monitoring rules are predefined for the instrument by a user. In some embodiments, standby monitoring rules are created by artificial intelligence that evaluates run data and establishes a new standby monitoring rule to be applied on the instrument.

In one embodiment, memory 15 may store the standby monitoring rules. The standby monitoring rules may relate to the control unit 13, the bays (e.g., bay 11), other components of the location device, other components of the system or combinations thereof.

As one example, a standby monitoring rule may include: When the location device experiences three consecutive errors, the bay is put on standby. In some embodiments, three consecutive errors occur when there are three consecutive invalid runs (that have not been processed by a previous auto-disabled event) in a row on a bay. In some embodiments, three consecutive errors occur when there are three consecutive invalid runs (that have not been processed by a previous auto-disabled event) in a row on a bay with certain validity codes. In some embodiments, three consecutive errors occur when there are three consecutive invalid runs (that have not been processed by a previous auto-disabled event) in a row on a bay with certain validity codes wherein the validity codes come from any combination of assay types. For example, all three validity codes may come from a first assay type. For example, all three validity codes may come from three different assay types. For example, a first validity code may come from a first assay type and two validity codes may come from a second assay type. For example, a first and second validity code may come from a first assay type and the third validity code may come from a second assay type. The assay types may be, for example, blood culture identification panels, respiratory panels, gastrointestinal panels, HCVg Test, Cystic Fibrosis Genotyping Test, Thrombophilia Risk Test, Warfarin Sensitivity Test, 2C19 Genotyping Test.

In some embodiments, once a bay is put on standby, the runs involved will be marked "processed" and excluded from the standby monitoring rule consideration in the future. In some embodiments, once a bay is put on standby, the runs involved will be marked "processed" and included in the standby monitoring rule consideration in the future.

In some embodiments, the standby monitoring rule is checked after each run, i.e., after each sample is processed by the instrument.

In some instances, the standby bay data is collected after a sample is processed. In some instances, the standby hay data is collected before a sample is processed. For example, if a bay fails to connect to two cartridges in a row, the standby monitoring rule is met and the bay is placed on standby. In some instances, failure to connect is determined by impedance data.

The standby bay monitoring rule (also referred to as threshold data) for a first location device may be the same as, more than and/or less than a standby bay monitoring rule for a second location device.

The standby bay threshold data for a first bay may be the same as, more than and/or less than a standby bay threshold for a second bay on that same device. The standby bay threshold data for a first bay may be the same as, more than and/or less than the standby bay threshold data for a first bay on a different device.

The standby bay threshold data may change over time.

The order of Blocks (processes) 54-512 is not limited to the order shown in FIG. 7 and may be performed in a different order based on design need. Further, one or more blocks may be skipped or omitted from FIG. 7 based on design need. e.g., Blocks (processes) 57, 59 and 510-512 may be skipped or omitted.
Modification.

In some embodiments, if a standby monitoring rule (e.g., threshold data) is violated, the processor 14 may optionally modify at least one setting of location device 12. In some embodiments, the processor may put a bay on standby when a standby rule is violated. In some embodiments, the processor may suggest a bay when a standby rule is not violated.

In some embodiments, the processor may modify one or more bay 11 settings and/or user interface 25 settings when a standby rule is violated. For example, the light on the bay door may be changed to indicate its standby status. For example, the light on the bay door may be changed to muted orange to indicate its standby status. For example, the icon color on the user interface corresponding to the bay may be changed to indicate its standby status. For example, the icon color on the user interface corresponding to the bay may be changed to muted orange to indicate its standby status. In addition to modifying the bay icon or bay door light color, in some embodiments, the processor may modify one or more bay 11 settings and/or user interface 25 settings when a standby bay rule is violated. For example, if a heater cannot reach the desired temperature, a bay fan may be turned on to improve temperature control.

In some embodiments, if the standby bay data is below a predetermined limit, the bay door is locked to prevent insertion of another sample. In some embodiments, if the standby bay data is below a predetermined limit, the bay door is not locked and if a sample is inserted into the bay, the bay processes it.

In some embodiments, if the standby bay data is above or below a predetermined limit or range, the bay remains available for use. In some embodiments, if the standby bay data is above or below a predetermined limit or range, the bay does not remain available for use, i.e., it is disabled.

In some embodiments, if a standby monitoring rule is not violated, the processor 14 may optionally modify at least one setting of location device 12. In some embodiments, the processor may modify one or more bay 11 settings and/or user interface 25 settings when a standby rule is not violated. For example, the light on the bay door may be changed to indicate its available status. For example, the light on the bay door may be changed to purple to indicate it is an available suggested bay to use. For example, the icon color on the user interface corresponding to the bay may be changed to indicate its suggest status. For example, the icon color on the user interface corresponding to the bay may be changed to purple to indicate its suggest status.

In some embodiments, when no standby monitoring rules are violated, the bay is suggested. In some embodiments, when no standby monitoring rules are violated, the bay is put on standby. In some embodiments, when no standby monitoring rules are violated, the bay status remains neutral, i.e., is not disabled, suggested or put on standby.
Alerts.

As shown in FIG. 7, at process 56, if processor 14 determines an issue does not exist (e.g., a standby rule is not violated), processor 14 may end the standby monitoring procedure. In some embodiments, when a standby rule is satisfied, a standby pass alert may be transmitted to user interface 25, the network 16, the remote monitoring center 17 and combinations thereof. The standby pass alert may indicate the one or more issues that were assessed have passed inspection or it may simply indicate that the system/bay is ready.

In some embodiments, when a standby rule is not satisfied, a standby fail alert may be transmitted to user interface 25, the network 16, the remote monitoring center 17 and combinations thereof. The standby fail alert may indicate the one or more issues that were assessed have failed inspection or it may simply indicate that the system/bay has been put on standby.

Processor 14 may determine whether to cause a standby alert. For example, processor 14 may determine whether to cause a standby alert based at least in part on a predetermined alert baseline that indicates a number of runs until one or more bays 11, location device 12 and/or control unit 13 are predicted to fail or be approaching a failure range. The standby alert baseline may vary depending on the type of alert, for example, 3 invalid runs in a row may send a standby failure alert but more than 50 low value signals may need to be sent before a standby failure alert is sent. The predetermined standby alert baseline for a first operational value may be the same as, more than and/or less than the standby alert threshold for a second operational value. The predetermined standby alert baseline for the user interface 25, location device 12, control unit 13 may be the same as, more than and/or less than each other. The predetermined standby alert baseline for a first location device may be the same as, more than and/or less than the standby alert baseline for a second location device. The predetermined standby alert baseline for a first bay may be the same as, more than and/or less than the standby alert baseline for a second bay on the same device.

Standby Analysis.

The standby analysis indicates whether the at least one of location device and/or bay is likely to operate within the failure range. The standby analysis indicates whether the at least one of location device and/or bay is likely to operate within the failure range within a predefined period of time.

The predefined period of time may be an hour, day, week and/or month, among other periods of time set by the user, network operator and/or diagnostic instrument provider company. The predefined period of time may be based on the number of samples processed, last 100, last 50, last 25, last 10, last 5, last 2, or last 1 or any other number set by the user, network operator and/or diagnostic instrument provider company.

For example, with respect to predicting failure based on proximate temperature, a system run at 5 degrees below room temperature may, over time, have a drop-in performance. Therefore, using aggregated data from multiple systems, if it is determined that a diagnostic instrument has been running for more than 24 hours in a laboratory that is 5 degrees below room temperature, it can be predicted that the diagnostic instrument may experience failures. Accordingly, it can be predicted when the diagnostic instrument will require technical support and/or service faster than an instrument operating in a room at room temperature. Additionally, a service provider (in some cases the diagnostic instrument provider) can evaluate why the system is operating in a room 5 degrees below room temperature and suggest a modification. For example, is the instrument near the A/C output? Could the diagnostic instrument be physically placed somewhere else to avoid standby failures? Note, this does not mean that the prediction is always correct. Nor does this mean that the prediction is always linear. In some implementations, it might be that operating the diagnostic instrument in a cold room accelerates damage over time.

In some embodiments, standby failures do not result in disable bay failures. In some embodiments, standby failures do not correlate to a disable bay failure in a linear fashion. In some embodiments, standby failures indicate an accelerated timeline of when the bay will fail and/or require service.

As an example, as a bay experiences wear, the number of volts needed to cross a resistor in order to heat the bay increases. While a voltage of V1 may pass a threshold test, a continued degradation in the resistor is a sign of trouble. If the diagnostic instrument can detect and log resistor degradation, it can disable a bay with resistor degradation, put a bay on standby if the resistor is degrading but is not yet below a threshold, or suggest the user use a different bay with a good resistor. Accordingly, while some systems may wait for a resistor to fail, with standby monitoring as described herein, the bay can be put on standby before it reaches a critical level, or bays with good resistors can be suggested for use over bays with degrading resistors. In this way, validity rates in the field will be improved because good bays are used over bad; good bays are used over bays that look like they are on the verge of becoming bad. In this way, no changes are made to the diagnostic assay to increase validity rates, avoiding the expense and effort of obtaining U.S. Food and Drug Administration (U.S. FDA) approval on a new assay design.

Similarly, as a bay ages, pumps may need to work harder to maintain pressure. While a pump may pass a threshold test, the effort needed for the pump to maintain pressure can be a sign of wear. If the diagnostic instrument can detect and log pump wear, it can disable a bay, put a bay on standby or suggest the user use a different bay. Indeed, any set of physically measurable control limits can be evaluated to see if the bay is experiencing wear.

As another example, target signal values may be acceptable but degrading. For example, the acceptable signal level threshold may be 600 nanoamps (na) but is typically 800 na. While a signal of 600 nanoamps may pass, a periodic but continued degradation is a sign of trouble. If the diagnostic instrument can detect and log signal degradation, it can disable a bay with signal degradation, put a bay on standby if the signal is degrading but is not yet below a threshold, or suggest the user use a different bay with good signal strength. Accordingly, while some systems may wait for signal level to reach the critical point, with standby monitoring as described herein, the bay can be put on standby before signal gets to a critical level, or bays with good signal can be suggested for use over bays with degrading signal.

As another example, it may be possible that a particular assay is more impacted by bay performance than others. For example, based on data run on that particular instrument, it may be determined that a gram-negative assay has a lower validity rate on a particular bay, but other assay types run fine on the bay. In such a situation, the bay may be disabled for all assays or just gram-negative assays. In such situations, when a new sample is scanned, the bay may process data about the assay type and disable a particular bay based on the assay type, i.e., the assay not functioning properly on the bay. In such situations, when a new sample is scanned, the bay may process data about the assay type and suggest a particular bay based on the assay type, i.e., the assay functioning properly on the bay. In this way a bay may be disabled and/or suggested based on the assay type.

In one embodiment, with potentially thousands of location devices 12 reporting signal degradation over time, to the network 16 or remote monitoring center 17, the remote monitoring center 17 can provide information back to the location device 12 stating that other systems have, on average, degraded when standby levels fall below a baseline and put a bay on standby. In some embodiments, if standby degradation is known, a bay can be disabled before it reaches a failure level and a sample is run with an invalid result.

In some embodiments, the standby bay threshold is a range, is a magnitude or intensity that must be exceeded for a certain condition to be met or is a combination thereof.

In another embodiment, in order to compensate for a first bay 11 that is predicted to fail, processor 14 may modify at least a second bay's settings based at least in part on the standby analysis of the first bay. For example, if bay 1's heaters are failing because the proximate temperature of the room is too low, the processor 14 may modify bay 2's settings so that the heaters turn on sooner in order to reach the desired temperature at the desired time point. As another example, if a first bay is experiencing communication failures, it can be predicted that the bay has a power issue. In such a situation, power to the entire tower may be compromised and each bay in the tower (column) may be disabled.

In another embodiment, processor 14 may determine whether to disable a bay or put it on standby based on the severity of the standby analysis. For example, if a bay has passed the threshold analysis but fails the standby analysis based on two or more values, the processor may disable a bay. Stated another way, if a bay has violated two or more standby rules, the processor 14 will disable the bay.

Suggest Monitoring Procedure

Figure 9:
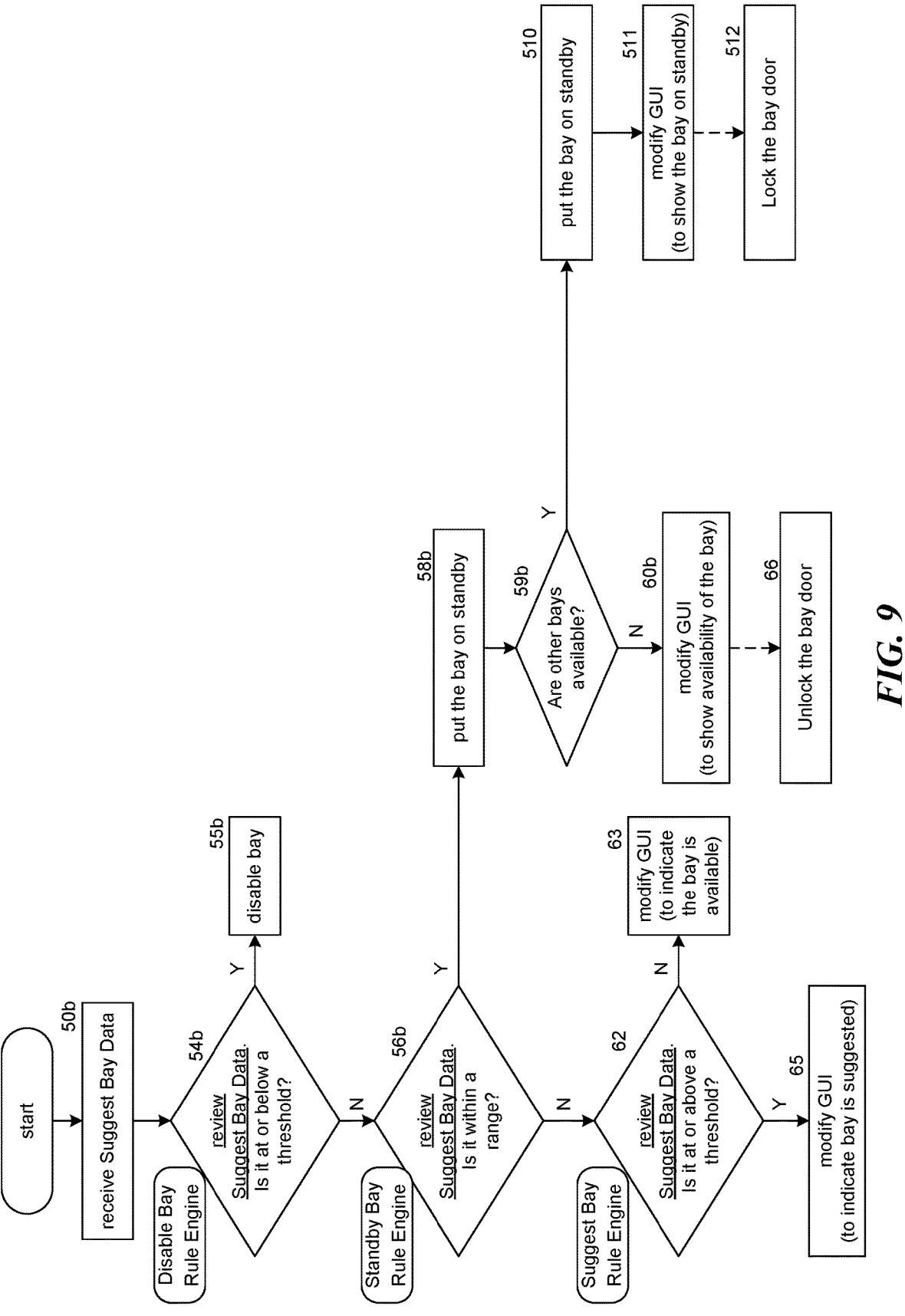
FIG. 9 is a flow chart of a suggest bay monitoring procedure in accordance with the principles of the present technology.

FIG. 9 shows an exemplary monitoring procedure of suggest rule engine 24b. In some embodiments, the outcome of a suggest rule analysis is to suggest a bay, put a bay on standby or disable a bay.

As shown in FIG. 9, the processor 14 receives suggest bay data from the control unit 13 (at process 50b). The processor 14 first reviews the suggest bay data (at process 54b) with the disable bay rule engine. If the suggest bay data is within a threshold range (e.g., at or below a predetermined threshold), the bay is disabled (at process 55b). The process 55b may be implemented in accordance with embodiments previously discussed in connection with the process 53 (in FIG. 6). In implementations of the process 54b, when the suggest bay data is not within the threshold range (e.g., above the predetermined limit), the processor 14 then reviews the suggest bay data (at process 56b) with the standby bay rule engine.

At process 56b, if the suggest bay data is within a certain range (e.g., below a predetermined limit), the bay is put on standby (at process 58b). The process 58b may be implemented in accordance with embodiments previously discussed in connection with processes at and after the process 58 (in FIG. 7).

On the other hand, at process 56b, if the suggest bay data is not within the range (e.g., above a predetermined limit), the suggest bay data is evaluated by the suggest rule engine (at process 62). At process 62, the suggest rule engine evaluates if the suggest bay data meets or fails to meet a threshold (e.g., threshold value or values). When the suggest rule engine determines the suggest bay data does not meet the threshold (e.g., below a predetermined limit), the user interface 25 (e.g., GUI) is modified to indicate that the bay is not suggested (at process 63). In some implementations of the process 63, for example, when the suggest bay data is below a predetermined limit, the sample is marked "processed." Whereas, for example, if the suggest rule engine determines the suggest bay data is at or above a predetermined limit, the user interface 25 (e.g., GUI) is modified to indicate that the bay is suggested (at process 65). In some implementations of process 65, for example, when the suggest bay data is above a predetermined limit, the sample is marked "processed."

In some embodiments, the suggest bay data is evaluated by the disable bay rule engine and/or standby bay rule engine before the suggest rule engine as set forth above. In some embodiments, the suggest bay data is evaluated by the suggest rule engine before the disable bay rule engine and/or disable bay rule engine. In some embodiments, the suggest bay data is only evaluated by the suggest rule engine.

In some embodiments, for example, when the suggest bay data is determined within the range (e.g., below a predetermined limit) at the process 56b by the standby bay rule engine and the bay is put on standby at the process 58b, the processor 14 evaluates whether there are other available bays at the process 59b. At process 59b, when it is determined there are no other available bays at the process 59b, the user interface 25 (e.g., GUI) is modified (at process 60b) to show that the bay is available (or suggested) to process another sample. For example, when it is determined that there are no other bays available (at process 59b), the system is configured to allow the user to run the sample in the bay. In some optional embodiments, for example, if the bay is put on standby at the process 58b and it is determined there are no other available bays, the bay door is unlocked (at process 66), e.g., if the bay had previously been put on standby and the bay door locked.

When, at process 59b, it is determined there are no other available bays, the bay is not suggested. When it is determined there are available bays at the process 59b, a bay is suggested, e.g., by modifying the user interface 25 (e.g., GUI) to identify the suggested bay. Also, when it is determined there are available bays at the process 59b, the processes 510, 511, and/or 512 may be implemented (as previously discussed).

In some embodiments, the suggest bay data is compared to at least one suggest baseline (e.g., suggest threshold data), and if it is below the suggest baseline, the bay is put on standby. In some embodiments, the suggest bay data is compared to at least one suggest baseline, and if it is above the suggest baseline, the bay is suggested. In some embodiments, the suggest bay data is compared to at least one suggest baseline, and if it is at or above the baseline, the bay is suggested.

In some embodiments, the suggest baseline data is based on the past performance of the bay being analyzed, past performance of other bays on the same instrument being analyzed, past performance of other bays on other instruments than the one being analyzed and combinations thereof.

The suggest baseline data indicates whether at least one of the bays is likely to operate within a desired range within a predefined window. The window can be a time frame or number of samples processed.

In some embodiments, the suggest bay procedure activates a bay previously disabled or put on standby.

Operational Suggest Monitoring Rule Engine and Software Suggest Monitoring Rule Engine.

In some embodiments, the processor 14 receives data from the control unit 13 (at process 50). In some embodiments, the processor 14 reviews the suggest bay data (at process 62) for operational issues in the operational suggest rule engine. In some embodiments, the processor 14 reviews the suggest bay data (at process 62) for software issues in the software suggest rule engine. In some embodiments, the processor 14 reviews the suggest bay data (at process 62) for operational issues in the operational suggest rule engine and software issues in the software suggest rule engine.

In some embodiments, the processor 14 reviews the suggest bay data (at process 62) for operational issues by evaluating if operating conditions meet operational suggest baseline(s). Operational suggest baselines include one or more predefined thresholds that indicate, when met, the device 12 or the bay's (e.g., bays 11*a*, 11*b* or 11*n*) hardware or firmware is currently likely to operate within desired parameters.

In some embodiments, the processor 14 reviews the suggest bay data (process 62) for software issues by evaluating if software suggest baseline(s) are met. Software suggest baselines include one or more predefined thresholds that indicate, when met, the device 12 or the bay's (e.g., bays 11*a*, 11*b* or 11*n*) hardware or firmware is currently likely to operate within desired parameters.

Suggest Monitoring Rules/Threshold Data Analysis.

Suggest monitoring rules (e.g., threshold data) are the rules which define the suggest monitoring procedure of suggest rule engine 24*b*. The outcome of a suggest rule is to either suggest a bay or disable a bay or put a bay on standby.

In some embodiments, suggest monitoring rules are predefined for the instrument by a user. In some embodiments, suggest monitoring rules are created by artificial intelligence that evaluates run data and establishes a new suggest monitoring rule to be applied on the instrument.

In one embodiment, memory 15 may store the suggest monitoring rules. The suggest monitoring rules may relate to the control unit 13, the bays (e.g., bay 11), other components of the diagnostic instrument, other components of the system or combinations thereof.

As one example, a suggest monitoring rule may include: When the location device experiences three consecutive valid runs, the bay is put on suggest. In some embodiments, three consecutive valid runs occur when there are three consecutive valid runs in a row on a bay. The runs may come from any combination of assay types. For example, all three validity codes may come from a first assay type. For example, all three validity codes may come from three different assay types. For example, a first validity code may come from a first assay type and two validity codes may come from a second assay type. For example, a first and second validity code may come from a first assay type and the third validity code may come from a second assay type. The assay types may be, for example, blood culture identification panels, respiratory panels, gastrointestinal panels, HCVg Test, Cystic Fibrosis Genotyping Test, Thrombophilia Risk Test, Warfarin Sensitivity Test, 2C19 Genotyping Test.

In some embodiments, once a bay is put on suggest, the runs involved will be marked "processed" and excluded from the suggest monitoring rule consideration in the future. In some embodiments, once a bay is put on suggest, the runs involved will be marked "processed" and included in the suggest monitoring rule consideration in the future.

In some embodiments, the suggest monitoring rule is checked after each run, i.e., after each sample is processed by the instrument.

In some instances, the suggest bay data is collected after a sample is processed. In some instances, the suggest bay data is collected before a sample is processed. For example, if a bay connects to three cartridges in a row, the suggest monitoring rule is met and the bay is placed on suggest. In some instances, connection is determined by impedance data.

The suggest bay monitoring rule (e.g., threshold data) for a first location device may be the same as, more than and/or less than a suggest bay monitoring rule for a second location device.

The suggest bay threshold for a first bay may be the same as, more than and/or less than a suggest bay threshold for a second bay on the same device. The suggest bay threshold for a first bay may be the same as, more than and/or less than a suggest bay threshold for a first bay on a different device.

The order of Blocks (processes) 54*b*-512 is not limited to the order shown in FIG. 9, and the blocks may be performed in a different order based on design need. Further, one or more blocks may be skipped or omitted from FIG. 9 based on design need, e.g., Blocks (processes) 54*b*, 56*b* and 510-512 may be skipped or omitted.

Modification.

In some embodiments, if a suggest monitoring rule (e.g., threshold data) is satisfied, the processor 14 may optionally modify at least one setting of location device 12. In some embodiments, the processor may put a bay on standby when a suggest rule is violated. In some embodiments, the processor may disable a bay when a suggest rule is violated.

In some embodiments, the processor may modify one or more bay 11 settings and/or user interface 25 settings when a suggest rule is satisfied. For example, the light on the bay door may be changed to indicate its suggest status. For example, the light on the bay door may be changed to muted orange to indicate its suggest status. For example, the icon color on the user interface corresponding to the bay may be changed to indicate its suggest status. For example, the icon color on the user interface corresponding to the bay may be changed to muted orange to indicate its suggest status.

In some embodiments, if a suggest monitoring rule is not violated, the processor 14 may optionally modify at least one setting of location device 12. In some embodiments, the processor may modify one or more bay 11 settings and/or user interface 25 settings when a suggest rule is not violated. For example, the light on the bay door may be changed to indicate its suggest status. For example, the light on the bay door may be changed to purple to indicate it is a suggested bay to use. For example, the icon color on the user interface corresponding to the bay may be changed to indicate its suggest status. For example, the icon color on the user interface corresponding to the bay may be changed to purple to indicate its suggest status.

In some embodiments, when no suggest monitoring rules are violated, the bay is suggested. In some embodiments, when suggest monitoring rules are violated, the bay status remains neutral, i.e., is not disabled, suggested or put on suggest. In some embodiments, when suggest monitoring rules are violated, the bay is disabled or put on standby.

Alerts.

As shown in FIG. 9, Block (process) 62, if processor 14 determines an issue does not exist (i.e., a suggest rule is not violated), processor 14 may end the suggest monitoring procedure. In some instances, when a suggest rule is satisfied, a suggest pass alert may be transmitted to user interface 25, the network 16, the remote monitoring center 17 and combinations thereof. The suggest pass alert may indicate the one or more issues that were assessed have passed inspection or it may simply indicate that the system/bay is ready.

In some instances, when a suggest rule is not satisfied, a suggest fail alert may be transmitted to user interface 25, the network 16, the remote monitoring center 17 and combinations thereof. The suggest fail alert may indicate the one or more issues that were assessed have failed inspection or it may simply indicate that the system/bay has been disabled.

A suggest rule threshold may be the same as, more than and/or less than a suggest rule threshold for a second bay on the same instrument. A suggest rule threshold may be the same as, more than and/or less than a suggest rule threshold for a second bay on a different instrument.

Suggest Analysis.

The suggest analysis indicates whether the at least one of location device and/or bay is likely to operate within the desired range. The suggest analysis indicates whether the at least one of location device and/or bay is likely to operate within the desired range within a predefined period of time.

The predefined period of time may be an hour, day, week and/or month, among other periods of time set by the user, network operator and/or diagnostic instrument provider company. The predefined period of time may be based on the number of samples processed, last 100, last 50, last 25, last 10, last 5, last 2, or last 1 or any other number set by the user, network operator and/or diagnostic instrument provider company.

For example, detecting controls is an important aspect of predicting the likelihood that a bay will process a sample correctly. Therefore, using aggregated data from multiple systems, if it is determined that a diagnostic instrument has failed to detect a control in the last three runs, it can be predicted that the diagnostic instrument bay may experience failures. Accordingly, it can be predicted when the diagnostic instrument bay will require technical support and/or service. Note, this doesn't mean that the prediction is always correct. Nor does this mean that the prediction is always linear. In some implementations, it might be that the failure to detect controls correlates to accelerated failure over time.

In another embodiment, to compensate for a first bay 11 that is predicted to operate correctly, processor 14 may modify at least a second bay's settings based at least in part on the suggest analysis of the first bay.

In another embodiment, processor 14 may determine whether to suggest a bay based on the intensity of the suggest analysis. For example, if a bay has failed a standby analysis but passed two or more suggest rules, the processor may nevertheless suggest the bay.

In some embodiments, the suggest bay threshold is a range, is a magnitude or intensity that must be exceeded for a certain condition to be met or is a combination thereof.

Evaluation Monitoring Procedure

In some embodiments, a single data set is evaluated by the different rule engines. For example, a single data set is evaluated by the disable bay rule engine, standby rule engine, suggest rule engine or combinations thereof (See FIG. 10.) For example, the first rule engine will look at the last ten runs and if four of the last ten runs are invalid, the bay is disabled, then the second rule engine will evaluate the data and if one to three of the last ten runs are invalid, the bay is put on standby, and then the third rule engine will evaluate the data and if none of the last ten runs are invalid, the bay is suggested. So rather than separately evaluating disable bay data, standby bay data and suggest bay data, one data set is evaluated by the different rule engines and compared to different thresholds (e.g., disable bay threshold, suggest bay threshold or standby bay threshold). Based on the one data set's pass or fail of the threshold, the processor performs a function such as modifies a GUI, modifies a bay door light, locks a bay door, unlocks a bay door or combinations thereof.

FIG. 10 shows an example embodiment of an evaluate monitoring procedure in accordance with the present technology. In some embodiments, the outcome of an evaluate rule analysis is to suggest a bay, put a bay on standby or disable a bay.

In some embodiments, the evaluate bay monitoring procedure is performed instead of the disable bay monitoring procedure, standby bay monitoring procedure, and/or suggest bay monitoring procedure. Yet, the evaluate bay monitoring procedure applies the same disable bay threshold, standby bay threshold, and/or suggest bay monitoring threshold as in those procedures.

In some embodiments of the evaluate monitoring procedure, the processor 14 receives evaluation data from the control unit 13 (at process 50c). The processor 14 reviews the evaluation data (71) by comparing it to the disable bay threshold. If the evaluation data meets the disable bay threshold (e.g., is at or above a predetermined disable bay threshold value(s)), the bay is disabled (at process 55c). The process 55c may be implemented in accordance with embodiments previously discussed in connection with the process 53 (in FIG. 6). In implementations of the process 71, when the evaluation data does not meet the disable bay threshold (e.g., not at or above a predetermined disable bay limit), the processor 14 compares the evaluation data to threshold standby bay data (at process 72).

At process 72, when the evaluation data is determined to not meet the standby bay threshold (e.g., above a predetermined standby baseline or range), the user interface 25 (e.g., GUI) is modified (at process 74) to show that the bay is suggested to process another sample. In implementations of process 72, when the evaluation data is determined to meet the standby bay threshold (e.g., below a predetermined standby limit or range), the bay is put on standby (at process 78). In some embodiments, at process 72, when the evaluation data is determined to meet the standby bay threshold (e.g., below a predetermined standby limit or range), the user interface 25 (e.g., GUI) is modified to indicate that the bay is not suggested (not shown).

When, at process 72 the evaluation data is determined to not meet the standby bay threshold (e.g., above a predetermined standby bay limit (baseline or range), the processor 14 implements process 73 to compare the evaluation data (56) to suggest bay threshold. In implementations of the process 73, when the evaluation data is determined to meet the suggest bay threshold (e.g., above a predetermined suggest bay threshold limit), the user interface 25 (e.g., GUI) is modified at process 65 to indicate that the bay is suggested. In implementations of the process 73, when the evaluation data is determined to not meet the suggest bay threshold (e.g., below the predetermined bay threshold suggest limit), the user interface 25 (e.g., GUI) is modified at process 63 to indicate that the bay is not suggested.

In some embodiments of the evaluate monitoring procedure, if the evaluation data does not meet the predefined or predetermined threshold(s) (e.g., disable bay threshold, suggest bay threshold, or standby bay threshold), the bay door is locked to prevent insertion of another cartridge. In some embodiments, for example, if the evaluation data meets the predefined or predetermined threshold(s), the bay door is not locked, and if a sample is inserted, the bay ejects the cartridge without processing it.

In some embodiments, if the evaluation data is below a predetermined limit, the bay door is disabled to prevent processing of another sample.

In some embodiments, if the evaluation data is above a predetermined limit (e.g., disable bay threshold, suggest bay threshold or standby bay threshold), the bay is not disabled, and the user interface 25 (e.g., GUI) is modified to indicate that the bay is ready to process another sample.

In some embodiments, the evaluation data is compared to at least one threshold (e.g., disable bay threshold, suggest bay threshold, standby bay threshold or combinations thereof), and if it is at or above the threshold, the sample is processed.

In some embodiments, the evaluate threshold is based on the past performance of the bay being analyzed. In some embodiments, the evaluate threshold is based on the past performance of other bays on the same instrument being analyzed. In some embodiments, the evaluate threshold is based on the past performance of other bays on other instruments than the one being analyzed. In some embodiments, the evaluate threshold is based on the past performance of the bay being analyzed, and/or the past performance of other bays on the same instrument being analyzed and/or the past performance of other bays on other instruments than the one being analyzed.

Assess Monitoring Procedure

In some embodiments, the instrument evaluates the one data set (referred to as run data) in one rule engine (referred to as the assess rule engine) to determine whether the bay should be put on standby, disabled or suggested (FIG. 11). For example, the bay will look at the last ten runs and if four of the last ten runs are invalid, the bay is disabled, if one to three of the last ten runs are invalid, the bay is put on standby, and if none of the last ten runs are invalid, the bay is suggested. So, rather than separately evaluating disable bay data, standby bay data and suggest bay data, one data set is evaluated by one rule engine and compared to different thresholds (e.g., disable bay threshold, suggest bay threshold or standby bay threshold). Based on the one data set's pass or fail of the threshold, the processor performs a function such as modifies a GUI or bay door light or locks a bay door, unlocks a bay door or combinations thereof.

FIG. 11 shows an example embodiment of an assess monitoring procedure in accordance with the present technology. In some embodiments, the outcome of an assess rule analysis is to suggest a bay, put a bay on standby, or disable a bay.

In some embodiments, the assess bay monitoring procedure is performed instead of the disable bay monitoring procedure, standby bay monitoring procedure and/or suggest bay monitoring procedure. Yet, the assess bay monitoring procedure applies the same disable bay threshold, standby bay threshold and/or suggest bay threshold as in those procedures.

In some embodiments, the processor 14 receives run data from the control unit 13 (at process 50d). The processor 14 reviews the run data (at process 84) by comparing it to the disable bay threshold. If the evaluation data meets the disable bay threshold (e.g., is at or above a predetermined disable bay threshold value or range), the bay is disabled (at process 85). In some implementations, the user interface 25 (e.g., GUI) is modified at process 85a to indicate the bay is disabled.

In implementations of process 84, if the run data is determined to not meet the disable bay threshold (e.g., below the predetermined disable bay threshold value or range), then the processor 14 compares the run data to standby bay threshold (e.g., is within a standby bay threshold data range). In implementations of the process 84 when the run data is determined to meet the standby bay threshold (e.g., within a predetermined standby threshold baseline or range), then the process 86 is implemented to put the bay on standby. In implementations of the process 84 when the run data is determined not to meet the standby bay threshold, the user interface 25 (e.g., GUI) may be modified to show that the bay is suggested to process another sample. In some embodiments, when the run data is determined to be put on standby at process 86, the user interface 25 (e.g. GUI) is modified at process 86a to indicate that the bay is not suggested.

In implementations of process 84 when the run data is determined to not meet the disable bay threshold and the standby bay threshold, then the processor 14 compares the run data to the suggest bay threshold data. In such implementations, if the run data is determined to meet the suggest bay threshold (e.g., at or above a predetermined suggest bay limit), the user interface 25 is modified to indicate that the bay is suggested (at process 87). In such implementations (when the run data is determined to meet the suggest bay threshold (e.g., at or above a predetermined suggest bay limit)), the user interface 25 (e.g., GUI) can be modified to indicate that the bay is suggested (at process 87a). In some implementations when the run data is determined not to meet the suggest bay threshold (e.g., below a predetermined suggest bay limit), the user interface 25 (e.g., GUI) can be modified to indicate that the bay is not suggested.

In some embodiments, if the run data is below a predetermined limit (e.g., disable bay threshold, suggest bay threshold or standby bay threshold), the bay door is locked to prevent insertion of another cartridge. In some embodiments, if the run data is below a predetermined limit, the bay door is not locked and if a sample is inserted the bay ejects the cartridge without processing it.

In some embodiments, if the run data is below a predetermined limit, the bay door is disabled to prevent processing of another sample.

In some embodiments, if the run data is above a predetermined limit (e.g., disable bay threshold, suggest bay threshold or standby bay threshold), the bay is not disabled, and the user interface 25 is modified to indicate that the bay is ready to process another sample.

In some embodiments, the run data is compared to at least one threshold (e.g., disable bay threshold, suggest bay threshold, standby bay threshold or combinations thereof), and if it is at or above the threshold, the sample is processed.

In some embodiments, the run threshold is based on the past performance of the bay being analyzed. In some embodiments, the run threshold is based on the past performance of other bays on the same instrument being analyzed. In some embodiments, the run threshold is based on the past performance of other bays on other instruments than the one being analyzed. In some embodiments, the run threshold is based on the past performance of the bay being analyzed, and/or the past performance of other bays on the same instrument being analyzed and/or the past performance of other bays on other instruments than the one being analyzed and/or combinations thereof.

In some embodiments, the outcome of an assess bay rule analysis is to either disable a bay or allow the bay to be used. In some embodiments, the outcome of an assess bay rule analysis is to either disable a bay, put a bay on standby or suggest a bay to be used.

As shown in FIG. 11, the processor 14 receives data from the control unit 13 (at process 50d). The processor 14 reviews the run data (at process 84). In some embodiments, the review means the processor 14 compares the run data (process 84) to threshold data from that bay, from other bays on the instrument, from other bays on other instruments or combinations thereof.

In some embodiments, the run data is compared to disable bay threshold data, standby bay threshold data or suggest bay threshold data (collectively, assess bay threshold data).

In some embodiments, if the run data is below a predetermined limit, the sample is marked "processed." In some embodiments, if the bay is disabled in response to run data, the results from the sample analyzed are still reported. In some embodiments, if the bay is disabled in response to run data, the results from the sample analyzed are not reported.

In some embodiments, if the run data is below a predetermined limit, the bay door is disabled to prevent processing of another sample. Disabling the bay may include failure to supply power to the bay, deletion of software protocols controlling the bay, disabling pumps, locking the bay door, ejecting a cartridge and combinations thereof.

In some instances, the run data is analyzed in the assess rule engine and the outcome is in a toggle relationship: if not disabled, then put on standby; if not put on standby, then disable; if not disabled, then suggest; if not suggested, then disable; if not put on standby, then suggest; if not suggested, then put on standby; if not disabled then suggest; if not suggested then disable.

In some embodiments, the threshold bay data is based on the past performance of the bay being analyzed, past performance of other bays on the same instrument being analyzed, past performance of other bays on other instruments than the one being analyzed, and combinations thereof.

In some embodiments, the threshold bay data is a range, is a magnitude or intensity that must be exceeded for a certain condition to be met, or is a combination thereof.

Operational Assess Bay Monitoring Rule Engine and Software Assess Bay Monitoring Rule Engine.

In some embodiments, as shown in FIG. 11, the processor 14 receives data from the control unit 13 (at process 50d). In some embodiments, the processor 14 reviews the run data (process 84) for operational issues in the operational assess bay rule engine, for software issues in the software assess rule engine and combinations thereof.

In some embodiments, the processor 14 reviews the assess bay data (run data) (at process 84) for operational issues by evaluating whether operating conditions meet operational assess bay baseline(s). Operational assess bay baselines include one or more predefined thresholds that indicate, when met, the location device 12 or the bay (e.g., bay 11a, 11b or 11n) currently has at least one hardware or firmware issue/problem.

In some embodiments, the processor 14 reviews the assess bay data (run data) (at process 84) for software issues by evaluating whether software assess bay baseline(s) are met. Software assess bay baselines include one or more predefined thresholds that indicate, when met, the location device 12 or the bay (e.g., bay 11a, 11b or 11n) currently has at least one software issue/problem.

In some embodiments, the assess bay threshold data will reveal that a bay in a particular location always performs poorly even when the bay is replaced. In such situations, the assess bay threshold data will always keep that bay disabled even if it passes all the rule engines.

Assess Bay Monitoring Rules/Threshold Data Analysis.

Assess bay monitoring rules (also referred to as threshold data) are the rules which define the assess bay monitoring procedure of assess rule engine 24c. In some embodiments, assess bay monitoring rules are predefined for the instrument by a user. In some embodiments, assess bay monitoring rules are created by artificial intelligence that evaluates run data and establishes a new assess bay monitoring rule to be applied on the instrument. In some embodiments, the assess bay monitoring rules are the disable bay monitoring rules, standby bay monitoring rules, suggest bay monitoring rules and combinations thereof or different bay monitoring rules.

In one embodiment, memory 15 may store the assess bay monitoring rules. The assess bay monitoring rules may relate to the control unit 13, the bays (e.g., bay 11), other components of the location device, other components of the system or combinations thereof.

As one example, an assess bay monitoring rule may include: When the location device experiences four consecutive errors, disable the bay.

Processor 14 performs the assess bay monitoring procedure and analysis. Processor 14 collects assess bay monitoring data.

The order of blocks is not limited to the order shown in FIG. 11 and may be performed in a different order based on design need. Further, one or more blocks may be skipped or omitted from FIG. 11 based on design need, e.g., Blocks 85-87 may be skipped or omitted.

Modification.

In some embodiments, if an assess bay monitoring rule is violated, the processor 14 may optionally modify at least one setting of location device 12. The light on the bay door may be changed to indicate its disabled status. For example, the light on the bay door may be changed to gray to indicate its disabled status. For example, the icon color on the user interface corresponding to the bay may be changed to indicate its disabled status. For example, the icon color on the user interface corresponding to the bay may be changed to gray to indicate its disabled status. For example, the bay door may be locked. For example, the power to the bay may be discontinued. In addition to modifying the bay icon or bay door light color, in some embodiments, the processor may modify one or more bay 11 settings and/or user interface 25 settings when an assess bay rule is violated. For example, if a heater cannot reach the desired temperature, a bay fan may be turned on to improve temperature control.

In some embodiments, if an assess bay monitoring rule (e.g., threshold data) is not violated, the processor 14 may optionally modify at least one setting of location device 12. In some embodiments, the processor may modify one or more bay 11 settings and/or user interface 25 settings when an assess bay rule is not violated. For example, the light on the bay door may be changed to indicate its status. For example, the light on the bay door may be changed to white to indicate its status is ready to process another sample. For example, the icon color on the user interface corresponding to the bay may be changed to white to indicate its ready to run status.

In some embodiments, when no assess bay monitoring rules are violated, the bay is suggested. In some embodiments, when no disable bay monitoring rules are violated, the bay is put on standby. In some embodiments, when no disable bay monitoring rules are violated, the bay status remains neutral, i.e., is not disabled, suggested or put on standby.

Alerts.

Referring back to FIG. 11, Block 54, if processor 14 determines an issue does not exist (e.g., a disable bay rule is not violated), processor 14 may end the assess bay monitoring procedure. In some instances, when an assess bay threshold rule is satisfied, an assess bay monitoring rule pass alert may be transmitted to user interface 25, the network 16, the remote monitoring center 17 and combinations thereof. The assess bay pass alert may indicate the one or more issues that were assessed have passed inspection or it may simply indicate that the system/bay is ready.

In some instances, when an assess bay rule is not satisfied, an assess bay fail alert may be transmitted to user interface 25, the network 16, the remote monitoring center 17 and combinations thereof. The assess bay fail alert may indicate the one or more issues that were assessed have failed inspection or it may simply indicate that the system/bay has been disabled.

In some embodiments, the run data set and evaluation data set are the same.

Behavioral Characteristics

In another embodiment, the monitoring procedures (disable bay monitoring procedures, standby monitoring procedures, suggest monitoring procedures, assess monitoring procedures and evaluate monitoring procedures) may not be based on instrument data, but on behavioral characteristics. For example, if the processor 14 determines that at least one behavioral characteristic of location-based instrument 12 is outside a baseline, it can suggest a bay, disable a bay or put a bay on standby. For example, if one bay is being used more frequently than another, i.e., top left compared to bottom right, the processor can suggest a different bay even though the bay being used has passed the disable and/or standby and/or suggest monitoring assessment(s).

A behavioral characteristic relates to instrument operation and/or function based on user input during a predefined time range and/or on predefined days in the week. For example, processor 14 may determine that bay number 1 is used every morning at 9:00 a.m., Monday through Friday. The at least one behavioral characteristic of the location-based system may indicate a window of time when the location-based system will suggest a different bay, i.e., suggest bay 6 at 9:00 a.m. Monday through Friday even though bay 1 does not violate any disable bay threshold data or standby threshold data. This way a particular bay does not get worn out before others.

Data Over Time

In one embodiment, the disable bay data, the standby bay data, the suggest bay data, run data, evaluate data and combinations thereof are based on data collected over time, i.e., data from more than one sample is assessed. For example, run data may include data from the last 5 samples processed, the last 10 samples processed, the last 50 samples processed, the last 100 samples processed, etc.

In one embodiment, the assess bay threshold data, the disable bay threshold data, the standby bay threshold data, the suggest bay threshold data and combinations thereof are based on data collected over time. For example, threshold data may include data from 5 samples processed, 10 samples processed, 50 samples processed, 100 samples processed, etc. Threshold data may be based on the past performance of the bay being analyzed, based on the past performance of other bays on the same instrument being analyzed, based on the past performance of other bays on other instruments than the one being analyzed, and combinations thereof.

Comparison Step

In some embodiments, the disable bay procedure, standby bay procedure, suggest bay procedure, evaluate bay procedure, assess bay procedure and combinations thereof (referred to as monitoring procedure) have an additional bay comparison step (not shown). In some embodiments, after a bay is determined to be disabled or put on standby or suggested, the monitor procedure then asks, "How does this bay compare to other bays?" As an example, if a diagnostic instrument has three bays, and the first bay has been disabled because of four invalid runs in a row, the second bay has been placed on standby because of two invalid runs in a row, and the third (present) bay has violated the behavioral characteristic disable threshold, the third bay is still the best bay of all the bays on the instrument because there is nothing inherently wrong with the performance of the bay except overuse, and it should not be disabled over the first and second bays. In this way, disabling a bay due to behavioral characteristics is not preferenced over disabling a bay due to a performance issue.

As another example, if a diagnostic instrument has three bays, and the first bay has been disabled because of four invalid runs in a row, the second bay has been placed on standby because of three invalid runs in a row, and the third (present) bay has one invalid run, then the third bay is the best bay of all the bays on the instrument and should be suggested over the first and second bays, or at least should not be placed on standby in order to drive usage to this best bay.

As another example, if a diagnostic instrument has three bays, and the first bay has been disabled because of four invalid runs in a row, the second bay has been placed on standby because of two invalid runs in a row, and the third (present) bay has no invalid runs, then the third bay is the best bay of all the bays on the instrument and should be suggested over the first and second bays.

In some embodiments, the bay comparison step for the monitor procedure is only performed if 10%, 20%, 30%, 40%, 50%, 60%, 70%, 80%, 90%, 95% or 100% of the bays have been disabled, placed on standby or a combination thereof Determination Step In some embodiments, processor 14 performs a "determination step" prior to the "receive data" process, in which it determines if self-monitoring is needed. If processor 14 determines not to initiate monitoring, processor 14 may loop and periodically perform the determination step. For example, the determination step for monitoring instrument health may be periodically repeated or may be continuous using a programmatic subroutine embedded within the general operating software.

In some embodiments, the location device 12 does not perform a "determine" step prior to "receive data" process, e.g., before process 51 (FIG. 6) or prior to process 54 (FIG. 7) or prior to process 54*b* (FIG. 9) or prior to process 71 (FIG. 10) or prior to process 84 (FIG. 11).

If processor 14 determines to initiate monitoring, processor 14 runs a monitoring process (such as disable bay monitoring process in FIG. 6). For example, processor 14 may initiate the disable bay monitoring process of disable bay monitoring rule engine 23 and/or standby monitoring process of standby monitoring rule engine 24*a* and/or suggest monitoring process of suggest monitoring rule engine 24*b* and/or assess monitoring process of assess monitoring rule engine 24*c*.

Analysis Algorithms

By way of non-limiting example, disable bay analysis algorithms, standby bay analysis algorithms, suggest bay analysis algorithms, and/or assess bay analysis algorithms may be implemented using data logic algorithms, statistical analysis, data analytics, and data manipulation in a manner known to those of ordinary skill in the art. This may include, for example, conventional software-based statistical analysis functions, financial functions, time-series functions, text string functions, grouping functions, etc. It could also incorporate software-based audio and video analytics capability (and the re-introduction of data outputted from such analytics back into the aforementioned functions).

In some embodiments, data analysis techniques that might be employed also include A/B testing, association rule learning, classification, cluster analysis, crowdsourcing, data fusion and integration, ensemble learning, genetic algorithms, machine learning, natural language processing, neural networks, pattern recognition, anomaly detection, standby modeling, regression, sentiment analysis, signal processing, supervised and unsupervised learning, simulation, time series analysis and visualization.

Monitoring Rules/Threshold Data

In some embodiments, monitoring rules (e.g., disable bay monitoring rules, standby monitoring rules, suggest monitoring rules or assess monitoring rules) may relate to any analysis of the bay's operation and may include: bay power status, ability to connect to a cartridge, impedance status, whether the bay heaters were able to reach desired temperatures, etc. Disable bay monitoring rules can monitor the hardware (actuators, bay door, pogo pins, etc.) to determine whether any hardware is not functioning properly or has been deactivated.

In some embodiments, monitoring rules (e.g., disable bay monitoring rules, standby monitoring rules, suggest monitoring rules or assess monitoring rules) may relate to any analysis of the assay's operation and may include: whether the signal strength is at or above a predetermined threshold, whether sample moved appropriately through the cartridge (moved appropriately may refer to speed, location, control, etc.), whether the controls were detected.

In some embodiments, monitoring rules (e.g., disable bay monitoring rules, standby monitoring rules, suggest monitoring rules or assess monitoring rules) may relate to any analysis of the instrument's operation and may also include: instrument power status, ability of the instrument to connect to the network, the status of operational software, the status of operational hardware, the status of operational firmware. For example, disable bay monitoring rules may monitor the software to determine whether any subsystems or rule engines are not functioning properly or have been deactivated.

In some embodiments, monitoring rules form the basis for threshold data. The bay factors for evaluate data, disable bay data, standby bay data, and suggest bay data are enumerated in Table 1.

TABLE 1

Bay Factors for Evaluate Data, Disable Bay Data, Standby Bay Data and Suggest Bay Data

|  | Disable bay | Put bay on standby | Suggest bay |
|---|---|---|---|
| Invalid runs | 4 out of the last 10 runs were invalid | 1-3 out of the last 10 runs were invalid | 0 out of the last 10 runs were invalid |
| Proximate bay temperature | 4 out of the last 10 runs had a proximate bay temperature 5 degrees above room temperature | 1-3 out of the last 10 runs had a proximate bay temperature 5 degrees above room temperature | All of the last 10 runs had a proximate bay temperature at room temperature |
| Monitoring | Violated more than 3 standby rules | Violated 1-2 standby rules | Violated no standby rules |
| Monitoring | Violated more than 3 suggest rules | Violated 1-2 suggest rules | Violated no suggest rules |
| Bay power | Off | | On |
| Bay connects to cartridge | Failed to connect in 4 out of the last 10 connection attempts (even if the connection | Failed to connect in 1-3 out of the last 10 connection attempts (even if the connection | All of the last 10 connection attempts were successful |

TABLE 1-continued

Bay Factors for Evaluate Data, Disable Bay Data, Standby Bay Data and Suggest Bay Data

|  | Disable bay | Put bay on standby | Suggest bay |
|---|---|---|---|
|  | attempts were with the same cartridge) | attempts were with the same cartridge) |  |
| Open detected | 4 out of the last 10 runs detected an open | 1-3 out of the last 10 runs detected an open | None of the last 10 runs detected an open |
| Short detected | 4 out of the last 10 runs detected a short | 1-3 out of the last 10 runs detected a short | None of the last 10 runs detected a short |
| Bay heaters failed to reach designated temperatures | Bay heaters failed to reach designated temperatures in 4 out of the last 10 runs | Bay heaters failed to reach designated temperatures in 1-3 out of the last 10 runs | All bay heaters reached designated temperatures in all of the last 10 runs |
| Calibration threshold | Not met | Met | Met |
| Bay communication | In 4 out of the last 10 runs, the bay failed to communicate with the software application | In 1-3 out of the last 10 runs, the bay failed to communicate with the software application | In all of the last 10 runs, the bay communicated with the software application |

The evaluate data, disable bay data, standby bay data and suggest bay data can be, but are not limited to, the factors set forth in Table 2.

TABLE 2

Instrument Factors for Evaluate Data, Disable Bay Data, Standby Bay Data and Suggest Bay Data

|  | Disable bay | Put bay on standby | Suggest a bay |
|---|---|---|---|
| Instrument power | Off | Intermittent | On |
| Connected to network | Not connected | Connected intermittently | Connected |

The evaluate data, disable bay data, standby bay data and suggest bay data can be, but are not limited to, the factors set forth in Table 3.

TABLE 3

Assay Factors for Evaluate Data, Disable Bay Data, Standby Bay Data and Suggest Bay Data

|  | Disable bay | Put bay on standby | Suggest a bay |
|---|---|---|---|
| Signal strength | 4 out of the last 10 runs have a signal strength below a threshold | 1-3 out of the last 10 runs have a degrading signal strength that is still above a threshold | All of the last 10 runs have a signal strength above a threshold |
| Detected controls | 4 out of the last 10 runs failed to detect the controls | 1-3 out of the last 10 runs failed to detect the controls | None of the last 10 runs failed to detect the controls |
| Sample movement | 4 out of the last 10 runs failed to move sample appropriately | 1-3 out of the last 10 runs failed to move sample appropriately | None of the last 10 runs failed to move sample appropriately |

The evaluate data, disable bay data, standby bay data and suggest bay data can be, but are not limited to, the factors set forth in Table 4.

US 12,586,679 B2

37

TABLE 4

Behavioral Factors for Evaluate Data, Disable Bay Data, Standby Bay Data and Suggest Bay Data

|  | Disable bay | Put bay on standby | Suggest a bay |
|---|---|---|---|
| Behavioral characteristic: top-left bay used first in the morning | Used first in the morning 3 days in a row | Used first in the morning 1-2 days in a row | Bay has not been used for more than 24 hours |

In some embodiments, disabled bays are inoperable. In some embodiments, disabled bays may not be used by the user. In some embodiments, disabled bays and bays on standby may not be used by the user. In some embodiments, disabled bays may be manually turned back on by a user.

In some embodiments, only suggested bays may be used. In some embodiments, suggested bays and bays on standby may be used.

In some embodiments, when a bay is on standby, it may still be used. In some embodiments, when a bay is on standby, it may not be used.

EXAMPLES

The system can be understood by the following numbered examples:

Example 1. A diagnostic instrument comprising: (a) a bay; (b) a control unit, the control unit comprising a disable bay rule engine, a standby rule engine and a suggest rule engine, wherein the disable bay monitoring rule engine produces disable bay data, the standby monitoring rule engine produces standby bay data and the suggest monitoring rule engine produces suggest bay data; and (c) a processor, wherein the processor determines whether the disable bay data, the standby bay data and the suggest bay data meet a predefined baseline; and in response to determining that the disable bay data does not meet the predefined baseline, the processor disables the bay.

Example 2. The diagnostic instrument of Example 1, wherein in response to determining that the disable bay data does not meet the predefined baseline, the processor modifies the GUI.

Example 3. The diagnostic instrument of Example 1 or 2, wherein in response to determining that the disable bay data does not meet the predefined baseline, the processor modifies the GUI by changing the color of a bay icon corresponding to the bay.

Example 4. The diagnostic instrument of Examples 1-3, wherein the bay further comprises a bay door and in response to determining that the disable bay data does not meet the predefined baseline, the processor locks the bay door.

Example 5. The diagnostic instrument of Examples 1-4, wherein the bay further comprises a bay light and in response to determining that the disable bay data does not meet the predefined baseline, the processor changes the color of the bay light.

Example 6. The diagnostic instrument of Examples 1-5, wherein in response to determining that the disable bay data does not meet the predefined baseline, the processor generates a disable bay fail alert.

Example 7. The diagnostic instrument of Examples 1-6, wherein the disable bay data is based on behavioral characteristics.

Example 8. The diagnostic instrument of Examples 1-7, wherein the disable bay data is based on data collected over time.

Example 9. A diagnostic instrument comprising: (a) a bay; (b) a control unit, the control unit comprising a disable bay rule engine wherein the disable bay monitoring rule engine produces disable bay data; and (c) a processor wherein the processor determines whether the disable bay data meets a predefined baseline; and, wherein in response to determining that the disable bay data does not meet the predefined baseline, the processor disables the bay.

Example 10. The diagnostic instrument of Example 9, wherein in response to determining that the disable bay data does not meet the predefined baseline, the processor modifies the GUI.

Example 11. The diagnostic instrument of Example 9 or 10, wherein in response to determining that the disable bay data does not meet the predefined baseline, the processor modifies the GUI by changing a color of a bay icon corresponding to the bay.

Example 12. The diagnostic instrument of Examples 9-11, wherein the bay further comprises a bay door and in response to determining that the disable bay data does not meet the predefined baseline, the processor locks the bay door.

Example 13. The diagnostic instrument of Examples 9-12, wherein the bay further comprises a bay light and in response to determining that the disable bay data does not meet the predefined baseline, the processor changes the color of the bay light.

Example 14. The diagnostic instrument of Examples 9-13, wherein in response to determining that the disable bay data does not meet the predefined baseline, the processor generates a disable bay fail alert.

Example 15. The diagnostic instrument of Examples 9-14, wherein the disable bay data is based on behavioral characteristics.

Example 16. The diagnostic instrument of Examples 9-15, wherein the disable bay data is based on data collected over time.

Example 17. A diagnostic instrument comprising: (a) a bay; (b) a control unit, the control unit comprising a standby rule engine wherein the standby monitoring rule engine produces standby bay data; and (c) a processor wherein the processor determines whether the standby bay data meets a predefined baseline, wherein in response to determining that the standby bay data does not meet the predefined baseline, the processor puts the bay on standby.

Example 18. The diagnostic instrument of Example 17, wherein in response to determining that the standby bay data does not meet the predefined baseline, the processor modifies the GUI.

Example 19. The diagnostic instrument of Example 18 or 17, wherein in response to determining that the standby bay data does not meet the predefined baseline, the processor modifies the GUI by changing the color of a bay icon corresponding to the bay.

Example 20. The diagnostic instrument of Examples 17-19, wherein the bay further comprises a bay door and in response to determining that the standby bay data does not meet the predefined baseline, the processor locks the bay door.

Example 21. The diagnostic instrument of Examples 17-20, wherein the bay further comprises a bay light and in response to determining that the standby bay data does not meet the predefined baseline, the processor changes the color of the bay light.

Example 22. The diagnostic instrument of Examples 17-21, wherein in response to determining that the standby bay data does not meet the predefined baseline, the processor generates a standby bay fail alert.

Example 23. The diagnostic instrument of Examples 17-22, wherein the standby bay data is based on behavioral characteristics.

Example 24. The diagnostic instrument of Examples 17-23, wherein the standby bay data is based on data collected over time.

Example 25. A diagnostic instrument comprising: (a) a bay; (b) a control unit, the control unit comprising a suggest rule engine wherein the suggest monitoring rule engine produces suggest bay data; and (c) a processor wherein the processor determines whether the suggest bay data meets a predefined baseline, wherein in response to determining that the suggest bay data meets the predefined baseline, the processor suggests the bay.

Example 26. The diagnostic instrument of Example 25, wherein in response to determining that the suggest bay data meets the predefined baseline, the processor modifies the GUI.

Example 27. The diagnostic instrument of Example 25 or 26, wherein in response to determining that the suggest bay data meets the predefined baseline, the processor modifies the GUI by changing the color of a bay icon corresponding to the bay.

Example 28. The diagnostic instrument of Examples 25-27, wherein the bay further comprises a bay light and in response to determining that the suggest bay data meets the predefined baseline, the processor changes the color of the bay light.

Example 29. The diagnostic instrument of Examples 25-28, wherein in response to determining that the suggest bay data meets the predefined baseline, the processor generates a suggest bay pass alert.

Example 30. The diagnostic instrument of Examples 25-29, wherein the suggest bay data is based on behavioral characteristics.

Example 31. A method for disabling a bay in a diagnostic instrument, the method comprising: (a) receiving disable bay data about at least one bay; (b) determining whether the disable bay data meets at least one predefined baseline; and (c) in response to determining that the disable bay data fails to meet the at least one predefined baseline, disabling the at least one bay.

Example 32. The method of Example 31, wherein in response to determining that the disable bay data does not meet the at least one predefined baseline, a processor modifies the GUI.

Example 33. The method of Example 31 or 32, wherein in response to determining that the disable bay data does not meet the at least one predefined baseline, a processor modifies the GUI by changing a color of a bay icon corresponding to the at least one bay.

Example 34. The method of Examples 31-33, wherein the at least one bay further comprises a bay door and in response to determining that the disable bay data does not meet the at least one predefined baseline, a processor locks the bay door.

Example 35. The method of Examples 31-34, wherein the bay further comprises a bay light and in response to determining that the disable bay data does not meet the at least one predefined baseline, the processor changes the color of the bay light.

Example 36. The method of Examples 31-35, wherein in response to determining that the disable bay data does not meet the at least one predefined baseline, a processor generates a disable bay fail alert.

Example 37. The method of Examples 31-36, wherein the disable bay data is based on behavioral characteristics.

Example 38. The method of Examples 31-37, wherein the disable bay data is based on data collected over time.

Example 39. A method for disabling a bay in a diagnostic instrument, the method comprising: (a) receiving disable bay data about a first bay; (b) determining whether the disable bay data meets at least one predefined baseline; and (c) in response to determining that the disable bay data fails to meet the at least one predefined baseline, disabling the bay.

Example 40. The method of Example 39, wherein in response to determining that the disable bay data does not meet the at least one predefined baseline, a processor modifies the GUI.

Example 41. The method of Example 39 or 40, wherein in response to determining that the disable bay data does not meet the at least one predefined baseline, the processor modifies the GUI by changing the color of a bay icon corresponding to the bay.

Example 42. The method of Examples 39-41, wherein the bay further comprises a bay door and in response to determining that the disable bay data does not meet the at least one predefined baseline, the processor locks the bay door.

Example 43. The method of Examples 39-42, wherein the bay further comprises a bay light and in response to determining that the disable bay data does not meet the at least one predefined baseline, the processor changes the color of the bay light.

Example 44. The method of Examples 39-43, wherein in response to determining that the disable bay data does not meet the at least one predefined baseline, the processor generates a disable bay fail alert.

Example 45. The method of Examples 39-44, wherein the disable bay data is based on behavioral characteristics.

Example 46. The method of Examples 39-45, wherein the disable bay data is based on data collected over time.

Example 47. A method for putting a bay in a diagnostic instrument on standby, the method comprising: (a) receiving standby bay data about a first bay; (b) determining whether the standby bay data meets at least one predefined baseline; and (c) in response to determining that the standby bay data fails to meet the at least one predefined baseline, putting the bay on standby.

Example 48. The method of Example 47, wherein in response to determining that the standby bay data does not meet the at least one predefined baseline, the processor modifies the GUI.

Example 49. The method of Example 47 or 48, wherein in response to determining that the standby bay data does not meet the at least one predefined baseline, the processor modifies the GUI by changing a color of a bay icon corresponding to the bay.

Example 50. The method of Examples 47-49, wherein the bay further comprises a bay door and in response to determining that the standby bay data does not meet the at least one predefined baseline, the processor locks the bay door.

Example 51. The method of Examples 47-50, wherein the bay further comprises a bay light and in response to determining that the standby bay data does not meet the at least one predefined baseline, the processor changes the color of the bay light.

Example 52. The method of Examples 47-51, wherein in response to determining that the standby bay data does not meet the at least one predefined baseline, the processor generates a disable bay fail alert.

Example 53. The method of Examples 47-52, wherein the standby bay data is based on behavioral characteristics.

Example 54. The method of Examples 47-53, wherein the standby bay data is based on data collected over time.

Example 55. A method for suggesting a bay in a diagnostic instrument, the method comprising: (a) receiving suggest bay data about a first bay; (b) determining whether the suggest bay data meets at least one predefined baseline; and (c) in response to determining that the suggest bay data meets the at least one predefined baseline, suggesting the bay.

Example 56. The method of Example 55, wherein in response to determining that the suggest bay data meets the at least one predefined baseline, the processor modifies the GUI.

Example 57. The method of Example 55 or 56, wherein in response to determining that the suggest bay data meets the at least one predefined baseline, the processor modifies the GUI by changing the color of a bay icon corresponding to the bay.

Example 58. The method of Examples 55-57, wherein the bay further comprises a bay door and in response to determining that the suggest bay data meets the at least one predefined baseline, the processor locks the bay door.

Example 59. The method of Examples 55-58, wherein the bay further comprises a bay light and in response to determining that the suggest bay data meets the at least one predefined baseline, the processor changes a color of the bay light.

Example 60. The method of Examples 55-59, wherein in response to determining that the suggest bay data meets the at least one predefined baseline, the processor generates a disable bay fail alert.

Example 61. The method of Examples 55-60, wherein the suggest bay data is based on behavioral characteristics.

Example 62. The method of Examples 55-61, wherein the suggest bay data is based on data collected over time.

Example 63. A method for disabling a diagnostic instrument on standby, the method comprising: (a) receiving run bay data about a first bay; (b) determining whether the run bay data meets at least one predefined baseline; and (c) in response to determining that the run bay data fails to meet the at least one predefined baseline, disabling the bay on standby.

Example 64. A method for suggesting a diagnostic instrument on standby, the method comprising: (a) receiving run bay data about a first bay; (b) determining whether the run bay data meets a first predefined baseline; (c) determining whether the run bay data meets a second predefined baseline; (d) determining whether the run bay data meets a third predefined baseline; and (e) in response to determining that the run bay data meets the first, second and third predefined baselines, suggesting the bay.

Example 65. The method of any one of Examples 1-64, wherein the run bay data is based on user behavioral characteristics.

Example 66. A monitoring system comprising a processing unit and a control unit, the control unit comprising a disable rule engine, wherein the disable rule engine produces disable data; and wherein the processor unit determines whether the disable data meets a predefined baseline.

Example 67. A graphical user interface comprising at least one icon corresponding to a processing unit, wherein the at least one icon changes from a first color to a second color in response to determining that processing unit data does not meet a predefined baseline.

Example 68. The graphical user interface of Example 67, wherein the first color and second color are different.

Example 69. A processing unit door lock comprising a door lock, wherein in response to determining that the processing unit data does not meet a predefined baseline, the door lock moves from a first position to a second position.

Example 70. The processing unit door lock of Example 69, wherein the first position of the door lock is unlocked, and the second position of the door lock is locked.

Example 71. A diagnostic instrument comprising a processing unit and a graphical user interface, the graphical user interface comprising at least one icon corresponding to the processing unit, wherein the at least one icon changes from a first color to a second color in response to determining that processing unit data does not meet a predefined baseline.

Example 72. The diagnostic instrument of Example 71, wherein the first color and second color are different.

Example 73. The diagnostic instrument or method of any of Examples 1-72, wherein monitoring of the bay will disable, put a bay (or plurality of bays) on standby and/or suggest one or more bays automatically.

Example 74. The diagnostic instrument or method of Example 73, wherein the diagnostic instrument or method automatically notifies users to be prompted to contact Technical Support for further investigation.

Example 75. The diagnostic instrument or method of Example 73 or 74, wherein the diagnostic instrument or method includes an option to override the bay disable, standby and/or suggest features.

Example B1. A method for disabling a processing unit in a diagnostic instrument, the method comprising: (a) receiving data about a first processing unit by a processor; (b) determining whether the data meets at least one predefined baseline; and (c) disabling the processing unit by the processor if the data fails to meet the at least one predefined baseline.

Example B2. The method of Example B1, wherein the diagnostic instrument further comprises a graphical user interface.

Example B3-A. The method of Example B2, wherein in response to determining that the data does not meet the at least one predefined baseline, the processor modifies the graphical user interface.

Example B3-B. The method of Example B2, wherein the graphical user interface has a processing unit icon corresponding to the processing unit, wherein the processing unit icon changes from a first color to a second color in response to determining that the data does not meet the at least one predefined baseline.

Example B4. The method of Example B1, wherein the first processing unit further comprises a door and the door locks in response to determining that the data does not meet the at least one predefined baseline.

Example B5. The method of Example B1, wherein the first processing unit further comprises a light and the light changes from a first color to a second color in response to determining that the data does not meet the at least one predefined baseline.

Example B6. The method of Example B1, wherein a fail alert is generated in response to determining that the data does not meet the at least one predefined baseline.

Example B7. The method of Example B1, wherein the data is based on behavioral characteristics.

Example B8. The method of Example B1, wherein disabling the processing unit comprises eliminating power to the processing unit, deleting software protocols controlling the processing unit, locking the processing unit door, ejecting a cartridge or combinations thereof.

Example B9. The method of Example B1, wherein the data is collected over time.

Example B10. A method for determining a status of a diagnostic instrument comprising: (a) displaying a first icon on the graphical user interface, the icon having a first color; (b) receiving data about a first processing unit by a processor; and (c) determining whether the data meets at least one predefined baseline; wherein the first color changes to a second color if the data fails to meet the at least one predefined baseline, wherein the second color reflects the status of the processing unit.

Example B11. The method of Example B10, further comprising: (a) displaying a second icon on the graphical user interface, the second icon having a first color; (b) receiving data about a second processing unit by a processor; and (c) determining whether the data meets at least one predefined baseline; wherein the second color changes to a third color if the data fails to meet the at least one predefined baseline, wherein the third color reflects the status of the processing unit.

Example B12. The method of Example B10, wherein the first processing unit is disabled after step (c).

Example B13. A method for increasing validity rates of a first diagnostic assay, the method comprising: (a) receiving data about a first processing unit in a first diagnostic instrument by a processor; (b) determining whether the data meets at least one predefined baseline; and (c) disabling the processing unit in the first diagnostic instrument if the data fails to meet the at least one predefined baseline.

Example B14. The method of Example B13, wherein the assay is a gram positive, gram negative fungal gastrointestinal or respiratory assay.

Example B15. The method of Example B13, wherein no changes are made to the diagnostic assay to increase the validity rates of the diagnostic assay.

Example B16. The method of Example B13, wherein the data is based on how the processing unit functions, how the diagnostic instrument functions, how the diagnostic assay functions, behavioral characteristics or combinations thereof.

Example B17. The method of Example B13, wherein the data is based on at least a first assay type, a second assay type, or both.

Example B18. The method of Example B13, wherein the data is not based on how the first diagnostic instrument or first processing unit functions.

Example B19. The method of Example B13, wherein the validity rates of the first diagnostic assay are increased but the validity rates of a second diagnostic assay are not increased.

Example B20. A diagnostic instrument comprising: (a) a processing unit for loading a sample; (b) a control unit for generating data; and (c) a processor, wherein the processor determines whether the data meets a predefined baseline; and in response to determining that the data does not meet the predefined baseline, the processor disables the processing unit.

Example B21. The diagnostic instrument of Example B20, wherein the control unit comprises a system for monitoring disable bay data.

Example B22. The diagnostic instrument of Example B20, wherein the control unit comprises a standby rule engine for producing standby bay data.

Example B23. The diagnostic instrument of Example B20, wherein the control unit comprises a suggest rule engine to produce suggest bay data.

Example B24. The diagnostic instrument of Example B20, wherein the processing unit further comprises a door and in response to determining that the data does not meet the predefined baseline, the door locks.

Example B25. The diagnostic instrument of Example B20, wherein the processing unit further comprises a light and in response to determining that the data does not meet the predefined baseline, the light changes color.

Example C1. A method for disabling a processing unit in a diagnostic instrument, the method comprising: receiving data about a first processing unit by a processor; determining whether the data meets at least one predefined baseline; and in response to determining that the data fails to meet the at least one predefined baseline, disabling the processing unit by the processor.

Example C2. The method of any of examples C1-C9, wherein the diagnostic instrument comprises a graphical user interface, and wherein in response to determining that the data fails to meet the at least one predefined baseline, the processor modifies the graphical user interface.

Example C3. The method of any of examples C1-C9, wherein the diagnostic instrument comprises a graphical user interface, and wherein the graphical user interface has a processing unit icon corresponding to the processing unit, the processing unit icon has a first color and wherein in response to determining that the data fails to meet the at least one predefined baseline, modifying the graphical user interface by the processor by changing the first color of the processing unit's icon to a second color wherein the first color and the second color are not the same.

Example C4. The method of any of examples C1-C9, wherein the processing unit further comprises a door and in response to determining that the data fails to meet the at least one predefined baseline, locking the door by the processor.

Example C5. The method of any of examples C1-C9, wherein the processing unit further comprises a light and in response to determining that the data fails to meet the at least one predefined baseline, changing the color of the light by the processor.

Example C6. The method of any of examples C1-C9, wherein in response to determining that the data fails to meet the at least one predefined baseline, generating a fail alert by the processor.

Example C7. The method of any of examples C1-C9, wherein the data is based on behavioral characteristics.

Example C8. The method of any of examples C1-C9, wherein disabling the processing unit comprises eliminating power to the processing unit, deletion of software protocols controlling the processing unit, locking the processing unit door, ejecting a cartridge and combinations thereof.

Example C9. The method of any of examples C1-C8, wherein the data is based on data collected over time.

Example C10. A method for updating a graphical user interface of a diagnostic instrument to reflect the status of a first processing unit on the diagnostic instrument, the method comprising: displaying a first icon on the graphical user interface, the first icon having a first color; receiving data about the first processing unit by a processor; determining whether the data meets at least one predefined baseline; and in response to determining that the data fails to meet the at least one predefined baseline, changing the first icon's color to a second color wherein the second color reflects the first processing unit's status.

Example C11. The method of any of examples C10-C14, further comprising displaying a second icon on the graphical user interface, the second icon having a first color; receiving second data about a second processing unit by a processor; determining whether the second data meets at least one predefined baseline; and in response to determining that the second data meets the at least one predefined baseline, changing the second icon's color to a third color wherein the third color reflects the second processing unit's status.

Example C12. The method of any of examples C10-C14, wherein the first processing unit is disabled and further comprising a second processing unit and the second processing unit is not disabled.

Example C13. The method of any of examples C10-C14, displaying a second icon on the graphical user interface, the second icon having a third color wherein the third color reflects the status of a second processing unit.

Example C14. The method of example C13 or any of examples C10-C14, wherein the first processing unit is disabled and the second processing unit is not disabled.

Example C15. A method for increasing validity rates of a first diagnostic assay, the method comprising: receiving data about a first processing unit in a first diagnostic instrument by a processor; determining whether the data meets at least one predefined baseline; and in response to determining that the data fails to meet the at least one predefined baseline, disabling the processing unit in the first diagnostic instrument by the processor, thereby increasing validity rates of the first diagnostic assay.

Example C16. The method of any of examples C15-C21, wherein the diagnostic assay is a gram positive, gram negative fungal gastrointestinal or respiratory assay Example C17. The method of any of examples C15-C21, wherein no changes are made to the diagnostic assay to increase the validity rates of the diagnostic assay.

Example C18. The method of any of examples C15-C21, wherein the data is based on how the processing unit functions, how the diagnostic instrument functions, how the diagnostic assay functions, behavioral characteristics or combinations thereof.

Example C19. The method of any of examples C15-C21, wherein the data is based on at least a first assay type and a second assay type.

Example C20. The method of any of examples C15-C21, wherein the data is not based on how the first diagnostic instrument or first processing unit functions.

Example C21. The method of any of examples C15-C21, wherein the validity rates of the first diagnostic assay are increased but the validity rates of a second diagnostic assay are not increased.

Example C22. A method, system or apparatus for assessing a bay of a diagnostic instrument as disclosed in this patent document.

Example C23. A method, system or apparatus for monitoring a diagnostic instrument to improve a field validity rate as disclosed in this patent document.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer-readable medium for execution by, or to control the operation of, data processing apparatus. The computer-readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer-readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a," "an" and "the" are intended to include the plural forms as well, unless the context clearly indicates otherwise. Additionally, the use of "or" is intended to include "and/or," unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

What is claimed is:

1. A diagnostic instrument, comprising:
a bay;
a control unit, the control unit comprising a disable bay rule engine, a standby bay monitoring rule engine, and a suggest bay rule engine, wherein the disable bay monitoring rule engine is configured to produce disable bay data, the standby bay monitoring rule engine is configured to produce standby bay data, and the suggest bay rule engine is configured to produce suggest bay data; and
a processor, wherein the processor is configured to determine whether one or more of the disable bay data, the standby bay data, or the suggest bay data meet a predefined baseline, wherein, in response to a determination by the processor that the disable bay data does not meet the predefined baseline, the processor is configured to disable the bay.

2. The diagnostic instrument of claim 1, wherein, in response to the determination by the processor that the disable bay data does not meet the predefined baseline, the processor is configured to modify a graphical user interface (GUI).

3. The diagnostic instrument of claim 2, wherein the processor is configured to modify the GUI by changing a color of a bay icon corresponding to the bay.

4. The diagnostic instrument of claim 1, wherein the bay further comprises a bay door, and wherein, in response to the determination by the processor that the disable bay data does not meet the predefined baseline, the processor is configured to lock the bay door.

5. The diagnostic instrument of claim 1, wherein the bay further comprises a bay light, and wherein, in response to the determination by the processor that the disable bay data does not meet the predefined baseline, the processor is configured to change a color of the bay light.

6. The diagnostic instrument of claim 1, wherein, in response to the determination by the processor that the disable bay data does not meet the predefined baseline, the processor is configured to generate a disable bay fail alert.

7. The diagnostic instrument of claim 1, wherein the disable bay data is based on one or more behavioral characteristics of the diagnostic instrument that includes a performance parameter associated with one or more operations performed by the diagnostic instrument based on a user input during a predefined time range.

8. A diagnostic instrument comprising a processing unit, and a graphical user interface, the graphical user interface comprising: at least one icon graphically corresponding to the processing unit, wherein the at least one icon is configured to change from a first color to a second color in response to a determination that an operation of the processing unit data does not meet a predefined baseline, wherein the processing unit comprises a processor and a memory, wherein the processing unit comprises a bay operable to receive an external cartridge to analyze a sample, and the processing unit includes a disable bay rule engine configured to produce disable bay data, a standby bay monitoring rule engine configured to produce standby bay data, and a suggest bay rule engine configured to produce suggest bay data, wherein the processor is configured to evaluate whether one or more of the disable bay data, the standby bay data, and the suggest bay data meet the predefined baseline, and
wherein the processor is configured to disable the bay, to put the bay on standby, or suggest the bay based on evaluation of the disable bay data, the standby bay data, and the suggest bay data, respectively.

9. The diagnostic instrument of claim 8, wherein the diagnostic instrument is configured to create a prompt to notify a user to override the disable the bay, the put the bay on standby, or the suggest the bay.

10. The diagnostic instrument of claim 8, wherein the diagnostic instrument is configured to automatically create a prompt to notify a user to contact Technical Support for further investigation of the diagnostic instrument.

11. The diagnostic instrument of claim 8, wherein disable bay rule engine comprises an operational threshold rule engine and/or software threshold rule engine.

* * * * *